United States Patent
Xu et al.

(10) Patent No.: US 10,398,100 B1
(45) Date of Patent: Sep. 3, 2019

(54) MARKERS ASSOCIATED WITH SUDDEN DEATH SYNDROME TOLERANCE IN SOYBEANS

(71) Applicant: Syngenta Participations AG, Basel (CH)

(72) Inventors: Zhanyou Xu, Slater, IA (US); Becky Welsh Breitinger, Research Triangle Park, NC (US); Harikrishnan Ramasubramaniam, Bay, AR (US); Ju-Kyung Yu, Slater, IA (US); Tracy Willaim Doubler, Slater, IA (US)

(73) Assignee: Syngenta Participations AG, Basel (CH)

( * ) Notice: Subject to any disclaimer, the term of this patent is extended or adjusted under 35 U.S.C. 154(b) by 16 days.

(21) Appl. No.: 15/345,103

(22) Filed: Nov. 7, 2016

Related U.S. Application Data

(60) Provisional application No. 62/254,748, filed on Nov. 13, 2015.

(51) Int. Cl.
| | | |
|---|---|---|
| *C12Q 1/6895* | (2018.01) | |
| *A01H 1/04* | (2006.01) | |
| *A01H 5/10* | (2018.01) | |
| *A01H 1/02* | (2006.01) | |

(52) U.S. Cl.
CPC ............... *A01H 1/04* (2013.01); *A01H 1/02* (2013.01); *A01H 5/10* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,300,541 B1 | 10/2001 | Lightfoot et al. | |
| 7,288,386 B2 | 10/2007 | Lightfoot et al. | |
| 7,767,882 B2 * | 8/2010 | Lu ............................ | A01H 1/04 435/6.16 |
| 7,902,337 B2 | 3/2011 | Lightfoot et al. | |
| 8,278,501 B2 | 10/2012 | Lu et al. | |
| 8,581,029 B2 | 11/2013 | Lu et al. | |
| 2002/0144310 A1 | 10/2002 | Lightfoot et al. | |
| 2006/0041954 A1 | 2/2006 | Lu et al. | |
| 2006/0288444 A1 | 12/2006 | McCarroll et al. | |
| 2008/0166699 A1 | 7/2008 | Baley et al. | |
| 2009/0208964 A1 | 8/2009 | McCarroll et al. | |
| 2010/0216129 A1 | 8/2010 | Lu et al. | |
| 2010/0240061 A1 | 9/2010 | Butruille et al. | |
| 2010/0275320 A1 | 10/2010 | Lightfoot et al. | |
| 2011/0252490 A1 | 10/2011 | Jenkinson | |
| 2012/0060240 A1 | 3/2012 | Lightfoot et al. | |
| 2012/0192315 A1 | 7/2012 | Lightfoot | |
| 2014/0041077 A1 | 2/2014 | Lu et al. | |
| 2014/0351997 A1 | 11/2014 | Lu et al. | |
| 2015/0259753 A1 | 9/2015 | Lu et al. | |

OTHER PUBLICATIONS

Swaminathan et al. Theor Appl Genet (2016)129:494-506.*
Triwitayakorn et al., "Genomic analysis of a region encompassing QRfs1 and QRfs2: genes that underlie soybean resistance to sudden death syndrome", Genome, vol. 48, pp. 125-138, 2005.
Njiti et al., Theor. Appl. Genet., "Common loci underlie field resistance to soybean sudden death syndrome in Forrest, Pyramid, Essex, and Douglas", vol. 104, pp. 294-300, 2002.
Hnetkovsky et al., "Genetic Mapping of Loci underlying Field Resistance to Soybean Sudden Death Syndrome (SDS)", Crop Science, vol. 36 pp. 393-400, 1996.
Chang et al., "Association of Loci Underlying Field Resistance to Soybean Sudden Death Syndrome (SDS) and Cyst Nematode (SCN) Race 3", Crop Science vol. 37, pp. 965-971, 1997.
Austeclinio et al., "Mapping and confirmation of a new sudden death syndrome resistance QTL on linkage group D2 from the soybean genotypes PI 567374 and 'Ripley'", Mol. Breeding vol. 20, pp. 53-62, 2007.
Wen et al., "Genome-wide association mapping of quantitative resistance to sudden death syndrome in soybean", BMC Genomics, vol. 15, 2014.

\* cited by examiner

*Primary Examiner* — Medina A Ibrahim
(74) *Attorney, Agent, or Firm* — Amy Krom

(57) ABSTRACT

The present invention relates to methods and compositions for identifying, selecting and/or producing an SDS tolerant soybean plant or germplasm. A soybean plant or germplasm that has been identified, selected and/or produced by any of the methods of the present invention is also provided. SDS tolerant soybean seeds, plants and germplasms are also provided.

7 Claims, No Drawings

Specification includes a Sequence Listing.

MARKERS ASSOCIATED WITH SUDDEN DEATH SYNDROME TOLERANCE IN SOYBEANS

RELATED APPLICATION INFORMATION

This Application claims the benefit of U.S. Provisional Application No. 62/254,748, filed 13 Nov. 2015, the contents of which are incorporated herein by reference.

FIELD OF THE INVENTION

The present invention relates to compositions and methods for identifying, selecting and producing Sudden Death Syndrome tolerant soybean plants.

BACKGROUND

Soybean Sudden Death Syndrome (SDS) is caused by a pathogenic fungal infection of *Fusarium solani*. Upon entering the roots and crowns of a soybean plant, the pathogen grows through the plant's vascular system, causing foliar scorch, sudden wilting and death.

At present, there is a dearth of suitable methods for preventing and managing SDS. Although fungicides may be effective in reducing population levels of the fungus, the use of fungicides does not always prevent SDS infections or achieve a complete reduction of SDS symptoms.

Identifying genes that enhances SDS tolerance of soybeans could lead to more efficient crop production by allowing for the identification, selection and production of soybean plants with enhanced SDS tolerance.

SUMMARY OF THE INVENTION

Compositions and methods for identifying, selecting and producing soybean plants with enhanced SDS tolerance are provided. SDS tolerant soybean plants and germplasms are provided.

In some embodiments, methods of identifying an SDS tolerant soybean plant or germplasm are provided. Such methods may comprise detecting, in the soybean plant or germplasm, a marker associated with enhanced SDS tolerance.

In some embodiments, methods of producing an SDS tolerant soybean plant are provided. Such methods may comprise detecting, in a soybean germplasm, the presence of a marker associated with enhanced SDS tolerance and producing a progeny plant from said soybean germplasm.

In some embodiments, methods of selecting an SDS tolerant soybean plant or germplasm are provided. Such methods may comprise crossing a first soybean plant or germplasm with a second soybean plant or germplasm, wherein the first soybean plant or germplasm comprises a marker associated with enhanced SDS tolerance, and selecting a progeny plant or germplasm that possesses the marker.

In some embodiments, methods of introgressing an allele associated with enhanced SDS tolerance into a soybean plant or germplasm are provided. Such methods may comprise crossing a first soybean plant or germplasm comprising an allele associated with enhanced SDS tolerance with a second soybean plant or germplasm that lacks said allele and optionally repeatedly backcrossing progeny plants comprising said allele with the second soybean plant or germplasm to produce an SDS tolerant soybean plant or germplasm comprising the allele associated with enhanced SDS tolerance. Progeny comprising the allele associated with enhanced SDS tolerance may be identified by detecting, in their genomes, the presence of a marker associated with said allele.

Further, some embodiments provided herein describe methods of selecting for soybean plants having enhanced SDS tolerance by characterizing a given plant's or population of plants' metabolite profile. For example, it was found that plants (not infected with SDS) having an increased level of Salicylic Acid were more likely to exhibit a SDS tolerant phenotype. Not to be limited by theory, this may indicate that these plants have an increased expression of genes in the SA pathway that may be a causative factor for this phenotype. Essentially, some embodiments herein demonstrate how one may use metabolite profiles to identify, select or characterize soy plants having enhanced SDS tolerance. Table 2 provides candidate genes that may be used to identify, select or create plants having increased resistance to SDS.

Soybean plants and/or germplasms identified, produced or selected by the methods of this invention are also provided, as are any progeny and/or seeds derived from a soybean plant or germplasm identified, produced or selected by these methods.

Non-naturally occurring soybean seeds, plants and/or germplasms comprising one or more markers associated with enhanced SDS tolerance are also provided.

A marker associated with enhanced SDS tolerance may comprise, consist essentially of or consist of a single allele or a combination of alleles at one or more genetic loci.

Additionally, some embodiments encompass the combination of soybean plants selected, identified or produced by the use of the markers described herein in combination with commercial fungicides for the control of a pathogen (e.g. SDS).

The foregoing and other objects and aspects of the present invention are explained in detail in the drawings and specification set forth below.

DETAILED DESCRIPTION OF THE INVENTION

The present invention provides compositions and methods for identifying, selecting and/or producing soybean plants with enhanced SDS tolerance, as well as soybean plants identified, selected and/or produced by a method of this invention. In addition, the present invention provides soybean plants and/or germplasms having within their genome and/or in their metabolomics profile one or more markers associated with enhanced SDS tolerance.

Definitions

Although the following terms are believed to be well understood by one of ordinary skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

As used herein, the terms "a" or "an" or "the" may refer to one or more than one. For example, "a" marker can mean one marker or a plurality of markers.

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

The term "consists essentially of" (and grammatical variants thereof), as applied to a polynucleotide sequence of this invention, means a polynucleotide sequence that consists of both the recited sequence (e.g., SEQ ID NO) and a total of ten or less (e.g., 1, 2, 3, 4, 5, 6, 7, 8, 9, or 10) additional nucleotides on the 5' and/or 3' ends of the recited sequence such that the function of the polynucleotide is not materially altered. The total of ten or less additional nucleotides includes the total number of additional nucleotides on both ends added together. The term "materially altered," as applied to polynucleotides of the invention, refers to an increase or decrease in ability to express the polynucleotide sequence of at least about 50% or more as compared to the expression level of a polynucleotide sequence consisting of the recited sequence.

As used herein, the term "allele" refers to one of two or more different nucleotides or nucleotide sequences that occur at a specific locus.

A marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced SDS tolerance" refers to a marker whose presence or absence can be used to predict whether and/or to what extent a plant will display an SDS tolerant phenotype.

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. Marker-assisted Backcrossing: A Practical Example, in TECHNIQUES ET UTILISATIONS DES MARQUEURS MOLECULAIRES LES COLLOQUES, Vol. 72, pp. 45-56 (1995); and Openshaw et al., Marker-assisted Selection in Backcross Breeding, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval defined by and including," used in reference to particular loci and/or alleles, refers to a chromosomal interval delimited by and encompassing the stated loci/alleles.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the phrase "introduced into a genome" refers to any known method one may employ to insert a given nucleotide sequence into the genome of an organism. For example, "introduced into the genome" of a soy plant would encompass traditional plant breeding methods, transgenic expression of a gene or gene editing methods (i.e. CRISPR, TALEN, etc) wherein said plant did not have said nucleotide sequence in its genome prior to said introduction.

As used herein, the terms "cultivar" and "variety" refer to a group of similar plants that by structural or genetic features and/or performance can be distinguished from other varieties within the same species.

As used herein, the terms "desired allele", "allele of interest" and "favorable allele" are used interchangeably to refer to an allele associated with a desired trait. In some embodiments, a "desired allele" and/or "allele of interest" may be associated with either an increase or a decrease of or in a given trait, depending on the nature of the desired phenotype. In some embodiments, a "desired allele" and/or "allele of interest" may be associated with a change in morphology, color, etc.

As used herein, the term "enhanced SDS tolerance" refers to an improvement, enhancement, or increase in a plant's ability to endure and/or thrive despite being infected with *Fusarium solani* as compared to one or more control plants (e.g., one or both of the parents, or a plant lacking a marker associated with enhanced SDS tolerance). Enhanced SDS tolerance includes any mechanism (other than whole-plant immunity or resistance) that reduces the expression of symptoms indicative of infection.

As used herein, the terms "elite" and "elite line" refer to any line that has resulted from breeding and selection for desirable agronomic performance. An elite line may be substantially homozygous. Numerous elite lines are available and known to those of skill in the art.

As used herein, the term "elite germplasm" refers to any germplasm that is derived from or is capable of giving rise to an elite plant.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm may refer to seeds, cells (including protoplasts and calli) or tissues from which new plants may be grown, as well as plant parts that can be cultured into a whole plant (e.g., stems, buds, roots, leaves, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" refers to a seed and/or plant produced when at least two genetically dissimilar parents are crossed.

As used herein, the term "inbred" refers to a substantially homozygous plant or variety. The term may refer to a plant or variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced SDS tolerance may be introgressed from a donor into a recurrent parent that is not SDS tolerant. The resulting offspring could then be repeatedly backcrossed and selected until the progeny possess the SDS tolerance allele(s) in the recurrent parent background.

As used herein, the term "linkage" refers to the degree with which one marker locus is associated with another marker locus or some other locus (for example, an SDS tolerance locus). The linkage relationship between a molecular marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

In some aspects of the present invention, it is advantageous to define a bracketed range of linkage, for example, from about 10 cM and about 20 cM, from about 10 cM and about 30 cM, or from about 10 cM and about 40 cM. The more closely a marker is linked to a second locus, the better an indicator for the second locus that marker becomes. Thus, "closely linked loci" such as a marker locus and a second locus display an inter-locus recombination frequency of about 10%, 9%, 8%, 7%, 6%, 5%, 4%, 3%, or 2% or less. In some embodiments, the relevant loci display a recombination frequency of about 1% or less, e.g., about 0.75%, 0.5%, 0.25% or less. Two loci that are localized to the same chromosome, and at such a distance that recombination between the two loci occurs at a frequency of less than about 10% (e.g., about 9%, 8%, 7%, 6%, 5%, 4%, 3%, 2%, 1%, 0.75%, 0.5%, or 0.25%, or less) may also be said to be "proximal to" each other. Since one cM is the distance between two markers that show a 1% recombination frequency, any marker is closely linked (genetically and physically) to any other marker that is in close proximity, e.g., at or less than about 10 cM distant. Two closely linked markers on the same chromosome may be positioned about 9, 8, 7, 6, 5, 4, 3, 2, 1, 0.75, 0.5 or 0.25 cM or less from each other.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., SDS tolerance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker or allele is located. In some embodiments, a locus may encompass one or more nucleotides.

As used herein, the terms "marker" and "genetic marker" are used interchangeably to refer to a nucleotide and/or a nucleotide sequence that has been associated with a phenotype, trait or trait form. In some embodiments, a marker may be associated with an allele or alleles of interest and may be indicative of the presence or absence of the allele or alleles of interest in a cell or organism. A marker may be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS) (Rafalski and Tingey, Trends in Genetics 9:275 (1993)), an amplified fragment length polymorphism (AFLP) (Vos et al., Nucleic Acids Res. 23:4407 (1995)), a single nucleotide polymorphism (SNP) (Brookes, Gene 234:177 (1993)), a sequence-characterized amplified region (SCAR) (Paran and Michelmore, Theor. Appl. Genet. 85:985 (1993)), a sequence-tagged site (STS) (Onozaki et al., Euphytica 138:255 (2004)), a single-stranded conformation polymorphism (SSCP) (Orita et al., Proc. Natl. Acad. Sci. USA 86:2766 (1989)), an inter-simple sequence repeat (ISSR) (Blair et al., Theor. Appl. Genet. 98:780 (1999)), an inter-retrotransposon amplified polymorphism (IRAP), a retrotransposon-microsatellite amplified polymorphism (REMAP) (Kalendar et al., Theor. Appl. Genet. 98:704 (1999)), a chromosome interval, or an RNA cleavage product (such as a Lynx tag). A marker may be present in genomic or expressed nucleic acids (e.g., ESTs). The term marker may also refer to nucleic acids used as probes or primers (e.g., primer pairs) for use in amplifying, hybridizing to and/or detecting nucleic acid molecules according to methods well known in the art. A large number of soybean molecular markers are known in the art, and are published or available from various sources, such as the SoyBase internet resource.

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. In some embodiments, marker genotypes are used to identify plants that will be selected for a breeding program or for planting.

In some embodiments, marker genotypes are used to identify plants that will not be selected for a breeding program or for planting (i.e., counter-selected plants), allowing them to be removed from the breeding/planting population.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein are also referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., SNP technology is used in the examples provided herein.

A "metabolite marker" refers to any metabolite (e.g. salicylic acid) which can be measured in a plant part and correlated to a plant phenotype and/or trait (e.g. SDS tolerance). One aspect of the invention is the correlation of increased levels of salicylic acid (SA) to SDS tolerance in a given soy line. The SA levels are considered increased in relation to a healthy soy plant not infected with a pathogen. One aspect of the invention is to create a metabolite profile for various soy lines (non-infected with SDS) and then selection of the lines having increased SA to carry forward to commercialization in a plant breeding program for SDS tolerance. Not to be limited by theory markers could further be developed that are linked to genes associated with the production of SA (e.g. GmSGT1-1, WRKY, UDP-glycosyltranferase, NPR1, MAP3K, PR1, MEKK1, MACSA, MOS3, pyruvate lyase, MKS1 and MPK3/6)

A "non-naturally occurring variety of soybean" is any variety of soybean that does not naturally exist in nature. A "non-naturally occurring variety of soybean" may be produced by any method known in the art, including, but not limited to, transforming a soybean plant or germplasm, transfecting a soybean plant or germplasm and crossing a naturally occurring variety of soybean with a non-naturally occurring variety of soybean. In some embodiments, a "non-naturally occurring variety of soybean" may comprise one of more heterologous nucleotide sequences. In some embodiments, a "non-naturally occurring variety of soybean" may comprise one or more non-naturally occurring copies of a naturally occurring nucleotide sequence (i.e., extraneous copies of a gene that naturally occurs in soybean). In some embodiments, a "non-naturally occurring variety of soybean" may comprise a non-natural combination of two or more naturally occurring nucleotide sequences (i.e., two or more naturally occurring genes that do not naturally occur in the same soybean).

As used herein, the term "offspring" plant refers to any plant resulting as progeny from a vegetative or sexual reproduction from one or more parent plants or descendants thereof. For instance an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings of F1s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

As used herein, the terms "phenotype," "phenotypic trait" or "trait" refer to one or more traits and/or manifestations of an organism. The phenotype can be a manifestation that is observable to the naked eye, or by any other means of evaluation known in the art, e.g., microscopy, biochemical analysis, or an electromechanical assay. In some cases, a phenotype or trait is directly controlled by a single gene or genetic locus, i.e., a "single gene trait." In other cases, a phenotype or trait is the result of several genes. It is noted that, as used herein, the term "SDS tolerance phenotype" takes into account environmental conditions that might affect SDS tolerance such that the effect is real and reproducible.

As used herein, the term "plant" may refer to a whole plant, any part thereof, or a cell or tissue culture derived from a plant. Thus, the term "plant" can refer to any of: whole plants, plant components or organs (e.g., roots, stems, leaves, buds, flowers, pods, etc.), plant tissues, seeds and/or plant cells. A plant cell is a cell of a plant, taken from a plant, or derived through culture from a cell taken from a plant. Thus, the term "soybean plant" may refer to a whole soybean plant, one or more parts of a soybean plant (e.g., roots, root tips, stems, leaves, buds, flowers, pods, seeds, cotyledons, etc.), soybean plant cells, soybean plant protoplasts and/or soybean plant calli.

As used herein, the term "polymorphism" refers to a variation in the nucleotide sequence at a locus, where said variation is too common to be due merely to a spontaneous mutation. A polymorphism can be a single nucleotide polymorphism (SNP) or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "population" refers to a genetically heterogeneous collection of plants sharing a common genetic derivation.

As used herein, the terms "progeny" and "progeny plant" refer to a plant generated from a vegetative or sexual reproduction from one or more parent plants. A progeny plant may be obtained by cloning or selfing a single parent plant, or by crossing two parental plants.

As used herein, the term "reference sequence" refers to a defined nucleotide sequence used as a basis for nucleotide sequence comparison. The reference sequence for a marker, for example, is obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

As used herein, the term "parental line" refers to a line for which a given plant is derived from. A "parental line" encompasses multiple generations.

As used herein, the terms "SDS tolerance" and "SDS tolerant" refer to a plant's ability to endure and/or thrive despite being infected with *Fusarium solani*. When used in reference to germplasm, the terms refer to the ability of a plant that arises from that germplasm to endure and/or thrive despite being infected with *Fusarium solani*. In some embodiments, infected SDS tolerant soybean plants may yield as well (or nearly as well) as uninfected soybean plants. In general, a plant or germplasm is labeled as "SDS tolerant" if it displays "enhanced SDS tolerance."

An "unfavorable allele" of a marker is a marker allele that segregates with the unfavorable plant phenotype, therefore providing the benefit of identifying plants that can be removed from a breeding program or planting.

Genetic Mapping

Genetic loci correlating with particular phenotypes, such as SDS tolerance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with enhanced SDS tolerance. Detection of these markers and/or other linked markers can be used to identify, select and/or produce SDS tolerant plants and/or to eliminate plants that are not SDS tolerant from breeding programs or planting.

Markers Associated with Enhanced SDS Tolerance

Markers associated with enhanced SDS tolerance are identified herein. A marker of the present invention may comprise a single allele or a combination of alleles at one or more genetic loci. For example, the marker may comprise one or more marker alleles located within a first chromosomal interval and one or more marker alleles located within a second chromosomal interval.

Markers of the present invention are described herein with respect to the positions of marker loci in a public build of the soybean genome (*Glycine max* version 1.01; U.S. Department of Energy Joint Genome Institute; hereinafter "Glyma 1.01"). See Table 1.

TABLE 1

Listing of Markers (i.e. QTLs) that associate with SDS

| Marker Locus | Physical Map Position in Glyma 1.01 | Favorable Marker Allele |
|---|---|---|
| SY0302B | (1) 2,699,816 | C |
| SY0303A | (1) 2,840,660 | T |
| IIY1810 | (1) 3,565,567 | |
| IIY15464 | (1) 4,194,972 | |
| IIY1670 | (1) 14,808,805 | |
| IIY1931 | (1) 44,037,641 | |
| IIY1933 | (1) 44,235,341 | |
| IIY1934 | (1) 44,319,352 | |
| IIY2054 | (1) 49,403,530 | |
| IIY2062 | (1) 49,768,758 | |
| IIY2227 | (1) 53,854,095 | |
| SY3859 | (1) 54,195,495 | |
| IIY2247 | (1) 54,312,240 | |
| IIY2255 | (1) 54,435,012 | |
| IIY2258 | (1) 54,483,533 | |
| IIY2261 | (1) 54,511,250 | |
| IIY2263 | (1) 54,522,175 | |
| IIY2271 | (1) 54,603,309 | |
| IIY2272 | (1) 54,612,083 | |
| IIY9346 | (2) 9,305,677 | |
| IIY9348 | (2) 9,321,563 | |
| IIY9352 | (2) 9,368,032 | |
| IIY9353 | (2) 9,424,159 | |
| IIY9354 | (2) 9,435,836 | |
| IIY9355 | (2) 9,438,183 | |
| IIY15804 | (2) 9,574,789 | |
| IIY9358 | (2) 9,577,168 | |
| IIY9359 | (2) 9,586,872 | |
| IIY9361 | (2) 9,610,601 | |
| IIY9373 | (2) 9,945,469 | |
| IIY8704 | (2) 10,039,622 | |
| IIY8730 | (2) 11,971,602 | |
| IIY8759 | (2) 14,303,993 | |
| IIY8766 | (2) 14,515,557 | |
| SY3863 | (2) 14,447,119 | |
| IIY8784 | (2) 15,316,814 | |
| IIY8795 | (2) 15,688,438 | |
| IIY8798 | (2) 15,712,952 | |
| IIY8799 | (2) 15,713,777 | |
| IIY8800 | (2) 15,723,632 | |
| IIY8801 | (2) 16,503,380 | |
| IIY8804 | (2) 17,026,649 | |
| IIY8921 | (2) 40,333,732 | |
| IIY8923 | (2) 40,414,232 | |
| IIY8924 | (2) 40,719,881 | |
| IIY15186 | (2) 40,720,806 | |
| IIY8933 | (2) 41,811,397 | |
| IIY8937 | (2) 41,830,194 | |
| IIY8962 | (2) 42,787,924 | |
| IIY16201 | (2) 42,788,887 | |
| IIY16157 | (2) 43,022,897 | |
| IIY8970 | (2) 43,135,032 | |
| SY1592AQ | (2) 43,158,480 | |
| IIY8979 | (2) 43,668,022 | |
| SY3862 | (2) 43,769,854 | |
| IIY16745 | (2) 44,511,240 | |
| IIY9018 | (2) 44,528,375 | |
| SY3867 | (2) 45,185,475 | |
| IIY9033 | (2) 45,189,862 | |
| IIY9034 | (2) 45,192,415 | |
| IIY9035 | (2) 45,227,272 | |
| IIY9037 | (2) 45,242,297 | |
| IIY14802 | (2) 45,305,571 | |
| IIY14967 | (2) 45,305,965 | |
| SY3868 | (2) 45,398,298 | |
| IIY9049 | (2) 45,598,187 | |
| SY1021AQ | (2) 45,947,482 | |
| IIY9065 | (2) 46,037,612 | |
| IIY9066 | (2) 46,041,049 | |
| IIY9068 | (2) 46,107,202 | |

TABLE 1-continued

Listing of Markers (i.e. QTLs) that associate with SDS

| Marker Locus | Physical Map Position in Glyma 1.01 | Favorable Marker Allele |
|---|---|---|
| IIY9070 | (2) 46,158,350 | |
| IIY9072 | (2) 46,159,916 | |
| IIY9073 | (2) 46,167,145 | |
| IIY16408 | (2) 46,188,333 | |
| IIY9075 | (2) 46,188,410 | |
| IIY9076 | (2) 46,190,483 | |
| IIY9077 | (2) 46,213,521 | |
| IIY9078 | (2) 46,243,455 | |
| IIY9082 | (2) 46,468,030 | |
| IIY9083 | (2) 46,477,155 | |
| IIY9084 | (2) 46,480,818 | |
| SY1307AQ | (2) 46,489,403 | |
| IIY9086 | (2) 46,556,123 | |
| IIY9087 | (2) 46,589,531 | |
| IIY9088 | (2) 46,593,815 | |
| IIY9091 | (2) 46,617,172 | |
| IIY9093 | (2) 46,809,860 | |
| IIY9094 | (2) 46,854,626 | |
| IIY9095 | (2) 46,862,160 | |
| IIY9096 | (2) 46,925,925 | |
| IIY9097 | (2) 46,935,192 | |
| IIY15356 | (2) 46,947,610 | |
| IIY16306 | (2) 46,975,391 | |
| IIY9098 | (2) 46,981,218 | |
| IIY9099 | (2) 46,996,655 | |
| IIY9101 | (2) 47,051,525 | |
| IIY9103 | (2) 47,087,664 | |
| IIY9108 | (2) 47,368,668 | |
| IIY9109 | (2) 47,373,605 | |
| IIY9110 | (2) 47,398,186 | |
| IIY9112 | (2) 47,465,750 | |
| IIY9115 | (2) 47,514,032 | |
| IIY9124 | (2) 48,215,047 | |
| IIY9125 | (2) 48,222,174 | |
| IIY9126 | (2) 48,296,011 | |
| IIY9127 | (2) 48,300,432 | |
| IIY9128 | (2) 48,327,101 | |
| IIY9145 | (2) 48,701,480 | |
| IIY9148 | (2) 48,723,822 | |
| IIY9207 | (2) 50,319,196 | |
| IIY9210 | (2) 50,342,827 | |
| IIY16117 | (2) 50,453,609 | |
| IIY10149 | (3) 20,980,164 | |
| IIY10153 | (3) 21,896,445 | |
| SY3869 | (3) 21,951,011 | |
| SY0060A | (3) 36,490,923 | G |
| SY0925AQ | (3) 38,076,587 | |
| IIY10319 | (3) 38,487,102 | |
| IIY10320 | (3) 38,511,822 | |
| IIY10348 | (3) 40,173,739 | |
| SY3871 | (3) 40,673,164 | |
| SY3874 | (3) 41,613,444 | |
| IIY10470 | (3) 44,916,159 | |
| IIY10490 | (3) 45,302,035 | |
| IIY10521 | (3) 45,957,040 | |
| IIY10522 | (3) 45,966,343 | |
| SY0906AQ | (3) 46,058,803 | C |
| IIY16323 | (4) 6,279,276 | |
| IIY11444 | (4) 9,828,784 | |
| IIY11449 | (4) 9,995,700 | |
| IIY10690 | (4) 11,151,450 | |
| IIY10692 | (4) 11,209,721 | |
| IIY10694 | (4) 11,222,048 | |
| IIY10695 | (4) 11,245,906 | |
| SY3872 | (4) 11,272,984 | |
| IIY10701 | (4) 11,530,760 | |
| IIY10703 | (4) 11,560,322 | |
| IIY14971 | (4) 11,567,805 | |
| IIY10708 | (4) 11,568,699 | |
| IIY10709 | (4) 11,569,766 | |
| IIY10710 | (4) 11,571,057 | |
| IIY10712 | (4) 11,596,883 | |
| IIY10895 | (4) 37,436,095 | |
| IIY10921 | (4) 39,247,964 | |
| IIY10936 | (4) 40,846,321 | |

TABLE 1-continued

Listing of Markers (i.e. QTLs) that associate with SDS

| Marker Locus | Physical Map Position in Glyma 1.01 | Favorable Marker Allele |
|---|---|---|
| SY3873 | (4) 41,045,743 | |
| SY3067 | (4) 14,594,788 | |
| SY3068 | (4) 14,745,457 | |
| SY3069 | (4) 14,824,630 | |
| SY3070 | (4) 14,827,787 | |
| SY3073 | (4) 14,988,435 | |
| SY3074 | (4) 14,997,903 | |
| SY3075 | (4) 15,495,892 | |
| IIY10979 | (4) 42,304,167 | |
| IIY10989 | (4) 42,844,073 | |
| SY0264AQ | (4) 42,935,605 | |
| IIY11006 | (4) 43,422,904 | |
| SY1708AQ | (4) 45,267,913 | |
| IIY11063 | (4) 45,327,708 | |
| IIY11066 | (4) 45,385,038 | |
| IIY11081 | (4) 45,885,566 | |
| SY3870 | (4) 46,743,233 | |
| IIY11183 | (4) 47,296,745 | |
| IIY11538 | (5) 27,483,709 | |
| IIY11540 | (5) 27,714,793 | |
| SY1744AQ | (5) 33,596,919 | |
| IIY11642 | (5) 34,534,101 | |
| IIY11643 | (5) 34,541,136 | |
| IIY11666 | (5) 35,125,112 | |
| IIY11667 | (5) 35,220,061 | |
| IIY11668 | (5) 35,236,755 | |
| IIY11674 | (5) 35,336,649 | |
| IIY11677 | (5) 35,364,565 | |
| IIY14919 | (5) 35,371,151 | |
| IIY14749 | (5) 35,371,192 | |
| IIY16560 | (5) 35,372,393 | |
| IIY11682 | (5) 35,374,308 | |
| SY0990AQ | (5) 35,461,364 | |
| IIY11699 | (5) 35,588,875 | |
| IIY11701 | (5) 35,600,630 | |
| IIY15941 | (5) 35,991,502 | |
| IIY11720 | (5) 36,252,629 | |
| IIY11724 | (5) 36,392,947 | |
| IIY11725 | (5) 36,394,107 | |
| IIY11727 | (5) 36,413,958 | |
| IIY11729 | (5) 36,428,793 | |
| SY0162AQ | (5) 36,447,100 | |
| IIY11764 | (5) 36,868,490 | |
| SY3875 | (5) 38,722,591 | |
| IIY11866 | (5) 38,765,188 | |
| IIY11872 | (5) 38,818,375 | |
| IIY11874 | (5) 38,860,597 | |
| IIY15261 | (5) 40,221,424 | |
| IIY11936 | (5) 40,358,849 | |
| IIY11937 | (5) 40,382,897 | |
| IIY11940 | (5) 40,418,062 | |
| IIY11942 | (5) 40,435,952 | |
| IIY16440 | (5) 40,475,521 | |
| IIY11946 | (5) 40,515,169 | |
| IIY11952 | (5) 40,702,652 | |
| IIY11955 | (5) 40,727,810 | |
| IIY11962 | (5) 40,771,270 | |
| IIY11963 | (5) 40,772,254 | |
| IIY11964 | (5) 40,810,803 | |
| IIY11965 | (5) 40,814,520 | |
| IIY15850 | (5) 40,837,883 | |
| IIY11972 | (5) 40,855,238 | |
| IIY15262 | (5) 40,908,217 | |
| IIY15057 | (5) 41,099,351 | |
| IIY12000 | (5) 41,255,280 | |
| IIY12004 | (5) 41,286,331 | |
| IIY12010 | (5) 41,316,061 | |
| IIY15663 | (5) 41,366,599 | |
| IIY12016 | (5) 41,366,902 | |
| IIY12017 | (5) 41,392,360 | |
| IIY12019 | (5) 41,394,645 | |
| IIY12021 | (5) 41,412,391 | |
| SY0169AQ | (5) 41,414,936 | |
| IIY12024 | (5) 41,444,691 | |
| IIY12162 | (6) 1,048,550 | |
| IIY12168 | (6) 1,064,830 | |
| IIY12477 | (6) 3,134,899 | |
| SY0019P | (6) 3,153,225 | |
| IIY12483 | (6) 3,372,305 | |
| IIY12716 | (6) 6,798,608 | |
| IIY12728 | (6) 7,214,433 | |
| IIY12746 | (6) 7,957,417 | |
| IIY12748 | (6) 7,963,470 | |
| SY1798AQ | (6) 8,243,123 | |
| IIY12771 | (6) 9,119,063 | |
| IIY12773 | (6) 9,187,422 | |
| IIY12775 | (6) 9,208,159 | |
| IIY12789 | (6) 9,741,555 | |
| IIY12179 | (6) 10,942,222 | |
| SY1291AQ | (6) 11,337,230 | |
| IIY12194 | (6) 11,338,307 | |
| IIY12195 | (6) 11,373,191 | |
| SY3876 | (6) 11,628,529 | |
| IIY12228 | (6) 12,263,022 | |
| IIY15819 | (6) 12,263,814 | |
| IIY12229 | (6) 12,264,454 | |
| IIY12230 | (6) 12,267,542 | |
| IIY16685 | (6) 12,272,007 | |
| SY1828AQ | (6) 12,334,119 | |
| IIY12232 | (6) 12,431,364 | |
| IIY12233 | (6) 12,449,407 | |
| SY3877 | (6) 12,453,786 | |
| SY1830AQ | (6) 12,461,998 | |
| SY1833AQ | (6) 12,680,000 | |
| SY0946A | (6) 12,950,865 | T |
| IIY12239 | (6) 12,954,507 | |
| IIY12241 | (6) 12,957,875 | |
| IIY12242 | (6) 12,963,848 | |
| IIY12245 | (6) 12,981,595 | |
| IIY12246 | (6) 12,982,501 | |
| IIY12247 | (6) 13,012,448 | |
| IIY15106 | (6) 13,079,446 | |
| IIY12248 | (6) 13,100,633 | |
| IIY12249 | (6) 13,176,003 | |
| IIY12251 | (6) 13,186,917 | |
| IIY12252 | (6) 13,195,525 | |
| IIY12253 | (6) 13,222,287 | |
| IIY12254 | (6) 13,265,999 | |
| IIY12255 | (6) 13,267,401 | |
| IIY12256 | (6) 13,289,794 | |
| IIY12257 | (6) 13,290,797 | |
| IIY12258 | (6) 13,292,299 | |
| IIY12262 | (6) 13,332,518 | |
| IIY12281 | (6) 13,515,069 | |
| IIY12317 | (6) 14,310,599 | |
| IIY12323 | (6) 14,426,454 | |
| IIY12359 | (6) 15,780,699 | |
| IIY12362 | (6) 15,889,111 | |
| IIY12363 | (6) 15,891,145 | |
| IIY12364 | (6) 15,892,738 | |
| IIY12365 | (6) 15,894,475 | |
| SY0916A | (6) 16,155,152 | T |
| IIY12382 | (6) 16,393,253 | |
| IIY12387 | (6) 16,538,845 | |
| IIY16688 | (6) 16,594,064 | |
| IIY12389 | (6) 16,594,230 | |
| SY1005A | (6) 27,068,199 | T |
| IIY13188 | (7) 5,556,758 | |
| IIY13216 | (7) 6,210,092 | |
| SY1014AQ | (7) 38,863,876 | |
| IIY13928 | (8) 7,463,529 | |
| SY0002AQ | (8) 8,219,011 | |
| SY0192AQ | (8) 10,850,225 | |
| IIY13424 | (8) 13,302,255 | |
| IIY13733 | (8) 41,236,594 | |
| IIY14943 | (8) 41,643,241 | |
| IIY13758 | (8) 42,927,508 | |
| IIY13784 | (8) 43,386,937 | |
| IIY13870 | (8) 46,592,248 | |
| IIY14676 | (9) 889,478 | |

TABLE 1-continued

Listing of Markers (i.e. QTLs) that associate with SDS

| Marker Locus | Physical Map Position in Glyma 1.01 | Favorable Marker Allele |
|---|---|---|
| IIY14008 | (9) 1,164,016 | |
| IIY14054 | (9) 1,762,844 | |
| IIY14210 | (9) 3,656,728 | |
| IIY14244 | (9) 3,812,299 | |
| SY0584AQ | (9) 4,223,863 | |
| IIY14564 | (9) 4,583,421 | |
| IIY14581 | (9) 5,015,481 | |
| IIY14583 | (9) 5,122,383 | |
| IIY14591 | (9) 5,400,132 | |
| IIY14592 | (9) 5,431,469 | |
| IIY14593 | (9) 5,433,753 | |
| SY3880 | (9) 5,501,736 | |
| SY3116 | (9) 6,113,727 | |
| SY3881 | (9) 6,439,663 | |
| IIY14633 | (9) 7,018,786 | |
| IIY14634 | (9) 7,020,353 | |
| IIY14637 | (9) 7,069,018 | |
| IIY14644 | (9) 7,339,963 | |
| IIY14645 | (9) 7,346,846 | |
| IIY14647 | (9) 7,422,843 | |
| IIY14648 | (9) 7,428,682 | |
| IIY16045 | (9) 7,472,956 | |
| IIY14652 | (9) 7,517,784 | |
| IIY14653 | (9) 7,686,312 | |
| IIY14655 | (9) 7,847,621 | |
| IIY16681 | (9) 7,898,892 | |
| IIY14657 | (9) 7,898,920 | |
| IIY14659 | (9) 7,979,695 | |
| IIY14660 | (9) 8,025,320 | |
| IIY14661 | (9) 8,244,372 | |
| IIY14662 | (9) 8,249,234 | |
| IIY14663 | (9) 8,284,675 | |
| IIY14664 | (9) 8,285,913 | |
| IIY14671 | (9) 8,852,613 | |
| IIY14672 | (9) 8,853,694 | |
| IIY16626 | (9) 8,854,633 | |
| IIY14674 | (9) 8,858,657 | |
| IIY14679 | (9) 9,581,771 | |
| IIY14684 | (9) 9,763,735 | |
| SY0592AQ | (9) 9,939,391 | |
| IIY13987 | (9) 10,104,471 | |
| IIY13988 | (9) 10,135,047 | |
| SY3879 | (9) 31,129,061 | |
| IIY15136 | (9) 40,648,771 | |
| IIY14334 | (9) 40,670,473 | |
| IIY14342 | (9) 40,733,360 | |
| SY3878 | (9) 41,073,831 | |
| IIY2856 | (10) 565,821 | |
| IIY2874 | (10) 724,389 | |
| SY1390AQ | (10) 1,044,193 | |
| IIY2406 | (10) 1,186,918 | |
| IIY2446 | (10) 1,576,632 | |
| IIY2453 | (10) 1,630,032 | |
| IIY2455 | (10) 1,648,679 | |
| IIY2457 | (10) 1,687,152 | |
| IIY15115 | (10) 2,309,535 | |
| IIY2476 | (10) 2,319,549 | |
| IIY2477 | (10) 2,366,401 | |
| IIY2478 | (10) 2,368,318 | |
| IIY2824 | (10) 5,158,618 | |
| IIY2411 | (10) 12,095,659 | |
| IIY2427 | (10) 13,242,046 | |
| IIY2546 | (10) 38,105,991 | |
| IIY2553 | (10) 38,659,036 | |
| IIY2557 | (10) 38,703,666 | |
| IIY2560 | (10) 38,745,750 | |
| SY3842 | (10) 38,762,082 | |
| IIY2563 | (10) 38,768,400 | |
| IIY2564 | (10) 38,803,983 | |
| IIY2565 | (10) 38,863,197 | |
| IIY2569 | (10) 38,890,422 | |
| IIY2570 | (10) 38,929,451 | |
| IIY2582 | (10) 39,370,450 | |
| IIY2584 | (10) 39,393,799 | |
| IIY2585 | (10) 39,395,867 | |
| IIY2588 | (10) 39,434,475 | |
| IIY2589 | (10) 39,436,275 | |
| SY1435AQ | (10) 43,812,363 | |
| SY38 | (10) 46,374,104 | |
| IIY2744 | (10) 47,982,549 | |
| IIY2748 | (10) 48,165,181 | |
| IIY2750 | (10) 48,261,299 | |
| SY2163AQ | (10) 48,282,455 | |
| IIY2752 | (10) 48,325,806 | |
| IIY2754 | (10) 48,360,055 | |
| IIY2756 | (10) 48,369,403 | |
| IIY2757 | (10) 48,383,456 | |
| IIY2758 | (10) 48,403,871 | |
| IIY2759 | (10) 48,409,261 | |
| IIY2761 | (10) 48,418,212 | |
| IIY2762 | (10) 48,422,497 | |
| IIY2763 | (10) 48,435,768 | |
| IIY2765 | (10) 48,451,452 | |
| IIY2766 | (10) 48,452,444 | |
| SY2164AQ | (10) 48,452,729 | |
| IIY2771 | (10) 48,736,012 | |
| IIY2772 | (10) 48,737,547 | |
| IIY15890 | (10) 48,810,142 | |
| IIY2775 | (10) 48,810,673 | |
| SY0940AQ | (10) 48,822,897 | |
| IIY15473 | (10) 48,898,112 | |
| IIY2776 | (10) 48,899,119 | |
| IIY2777 | (10) 48,929,490 | |
| IIY2779 | (10) 48,936,653 | |
| IIY15065 | (10) 48,937,502 | |
| IIY2787 | (10) 49,569,904 | |
| IIY2803 | (10) 49,999,198 | |
| IIY3192 | (11) 59,512 | |
| IIY3259 | (11) 73,971 | |
| SY3857 | (11) 4,812,872 | |
| IIY3171 | (11) 5,088,630 | |
| IIY3191 | (11) 5,934,662 | |
| IIY16277 | (11) 6,036,589 | |
| IIY3224 | (11) 6,496,150 | |
| IIY3246 | (11) 7,102,091 | |
| IIY3249 | (11) 7,138,061 | |
| IIY3263 | (11) 7,596,095 | |
| IIY3264 | (11) 7,604,438 | |
| SY3850 | (11) 9,276,400 | |
| IIY3364 | (11) 9,984,007 | |
| SY3851 | (11) 10,317,234 | |
| IIY3038 | (11) 36,593,448 | |
| SY3846 | (11) 36,598,624 | |
| IIY15827 | (11) 37,418,427 | |
| IIY3805 | (12) 398,384 | |
| IIY3986 | (12) 953,856 | |
| IIY3372 | (12) 1,031,810 | |
| SY0479AQ | (12) 1,083,728 | |
| IIY3592 | (12) 3,318,677 | |
| SY0974AQ | (12) 3,377,537 | |
| SY2260AQ | (12) 4,707,399 | |
| SY2279AQ | (12) 34,175,881 | |
| IIY3637 | (12) 34,697,261 | |
| IIY3643 | (12) 34,947,739 | |
| IIY3644 | (12) 34,949,949 | |
| IIY3647 | (12) 35,069,294 | |
| SY0496AQ | (12) 35,196,099 | |
| IIY3652 | (12) 35,231,899 | |
| IIY3661 | (12) 35,337,190 | |
| IIY3666 | (12) 35,397,116 | |
| IIY3670 | (12) 35,450,530 | |
| IIY3671 | (12) 35,475,655 | |
| IIY3728 | (12) 37,120,553 | |
| SY3843 | (12) 37,950,570 | |
| IIY3746 | (12) 37,952,294 | |
| IIY3748 | (12) 37,975,292 | |
| IIY3749 | (12) 37,977,695 | |
| IIY3753 | (12) 38,040,602 | |
| IIY3754 | (12) 38,043,920 | |
| SY3852 | (12) 38,052,909 | |

TABLE 1-continued

Listing of Markers (i.e. QTLs) that associate with SDS

| Marker Locus | Physical Map Position in Glyma 1.01 | Favorable Marker Allele |
|---|---|---|
| IIY3760 | (12) 38,143,929 | |
| SY0500AQ | (12) 38,202,779 | |
| SY3853 | (13) 4,770,991 | |
| IIY4730 | (13) 5,059,265 | |
| SY2311AQ | (13) 6,810,239 | |
| IIY4780 | (13) 7,718,677 | |
| IIY4781 | (13) 7,719,764 | |
| IIY4783 | (13) 7,754,866 | |
| IIY4788 | (13) 7,983,753 | |
| SY1032A | (13) 20,484,995 | A |
| SY3848 | (13) 24,858,677 | |
| IIY15143 | (13) 25,360,790 | |
| SY3854 | (13) 27,116,538 | |
| IIY4216 | (13) 28,032,256 | |
| IIY4222 | (13) 28,128,218 | |
| IIY4233 | (13) 28,314,950 | |
| IIY15966 | (13) 28,332,900 | |
| IIY14849 | (13) 28,390,173 | |
| SY3883 | (13) 29,458,130 | |
| SY0132A | (13) 29,825,027 | T |
| SY0422A | (13) 29,825,175 | C |
| IIY4284 | (13) 30,265,276 | |
| SY0080A | (13) 30,457,450 | T |
| IIY4307 | (13) 30,857,311 | |
| SY0421A | (13) 30,965,274 | I |
| IIY4428 | (13) 33,627,404 | |
| SY38 | (13) 34,700,965 | |
| IIY15145 | (13) 34,724,754 | |
| IIY4452 | (13) 34,725,792 | |
| IIY4453 | (13) 34,750,188 | |
| IIY4455 | (13) 34,806,626 | |
| IIY4457 | (13) 34,829,333 | |
| IIY4458 | (13) 34,845,145 | |
| IIY4460 | (13) 34,866,807 | |
| IIY4461 | (13) 34,872,362 | |
| IIY4462 | (13) 34,937,502 | |
| IIY4467 | (13) 34,969,991 | |
| IIY4468 | (13) 34,972,922 | |
| IIY4469 | (13) 34,983,320 | |
| IIY4470 | (13) 34,985,495 | |
| IIY4471 | (13) 34,994,997 | |
| IIY4473 | (13) 35,045,474 | |
| IIY4474 | (13) 35,049,090 | |
| IIY4475 | (13) 35,072,030 | |
| IIY4477 | (13) 35,134,459 | |
| IIY4479 | (13) 35,140,845 | |
| IIY4480 | (13) 35,172,504 | |
| IIY4487 | (13) 35,549,787 | |
| IIY4493 | (13) 35,823,512 | |
| IIY4494 | (13) 35,835,159 | |
| SY1099AQ | (13) 35,909,694 | |
| IIY4500 | (13) 35,930,972 | |
| IIY4502 | (13) 35,941,743 | |
| IIY4505 | (13) 35,952,815 | |
| IIY15728 | (13) 36,145,433 | |
| IIY4515 | (13) 36,188,290 | |
| IIY4518 | (13) 36,258,902 | |
| IIY4520 | (13) 36,281,216 | |
| IIY4521 | (13) 36,349,245 | |
| IIY4522 | (13) 36,370,932 | |
| IIY4523 | (13) 36,394,126 | |
| SY0432AQ | (13) 36,567,182 | |
| SY3841 | (13) 36,639,889 | |
| IIY4533 | (13) 36,667,660 | |
| IIY4535 | (13) 36,692,058 | |
| IIY4536 | (13) 36,708,599 | |
| IIY4537 | (13) 36,717,877 | |
| SY2345AQ | (13) 36,719,523 | |
| SY3882 | (13) 36,792,738 | |
| IIY4539 | (13) 36,820,495 | |
| IIY4542 | (13) 36,848,791 | |
| SY3855 | (13) 36,860,098 | |
| SY3856 | (13) 36,866,030 | |
| IIY4584 | (13) 38,426,368 | |
| IIY4609 | (13) 39,237,614 | |

TABLE 1-continued

Listing of Markers (i.e. QTLs) that associate with SDS

| Marker Locus | Physical Map Position in Glyma 1.01 | Favorable Marker Allele |
|---|---|---|
| IIY4852 | (14) 126,668 | |
| IIY4927 | (14) 256,964 | |
| SY3847 | (14) 531,934 | |
| IIY5252 | (14) 637,841 | |
| SY0118B | (14) 807,326 | C |
| IIY4812 | (14) 1,017,340 | |
| IIY4828 | (14) 1,131,215 | |
| IIY4842 | (14) 1,219,464 | |
| SY0121A | (14) 1,359,785 | C |
| IIY4871 | (14) 1,629,681 | |
| IIY4873 | (14) 1,656,532 | |
| IIY4874 | (14) 1,671,631 | |
| SY0125B | (14) 1,877,090 | G |
| IIY4881 | (14) 1,895,486 | |
| IIY4883 | (14) 1,900,452 | |
| IIY4884 | (14) 1,902,262 | |
| IIY4887 | (14) 1,913,539 | |
| IIY4888 | (14) 1,920,147 | |
| SY0126C | (14) 2,104,413 | A |
| IIY4895 | (14) 2,132,299 | |
| IIY4896 | (14) 2,154,500 | |
| IIY4897 | (14) 2,168,760 | |
| IIY4901 | (14) 2,248,014 | |
| IIY4932 | (14) 2,754,212 | |
| IIY4933 | (14) 2,755,026 | |
| IIY4934 | (14) 2,757,122 | |
| IIY4936 | (14) 2,762,103 | |
| IIY4937 | (14) 2,763,974 | |
| IIY4938 | (14) 2,771,681 | |
| IIY15795 | (14) 2,774,226 | |
| IIY4939 | (14) 2,776,022 | |
| IIY4940 | (14) 2,780,199 | |
| IIY4941 | (14) 2,802,474 | |
| IIY16317 | (14) 2,804,098 | |
| IIY4942 | (14) 2,804,742 | |
| IIY4943 | (14) 2,810,853 | |
| IIY4953 | (14) 2,926,741 | |
| IIY4954 | (14) 2,927,724 | |
| IIY4955 | (14) 2,937,477 | |
| IIY16493 | (14) 2,956,918 | |
| IIY4958 | (14) 2,957,404 | |
| IIY4959 | (14) 2,984,462 | |
| SY2366AQ | (14) 3,025,155 | |
| IIY4969 | (14) 3,048,459 | |
| IIY15150 | (14) 3,315,202 | |
| IIY16397 | (14) 3,344,943 | |
| IIY4985 | (14) 3,345,600 | |
| IIY4989 | (14) 3,357,221 | |
| IIY4992 | (14) 3,361,319 | |
| IIY4994 | (14) 3,412,862 | |
| IIY4995 | (14) 3,417,140 | |
| IIY4997 | (14) 3,429,711 | |
| IIY4999 | (14) 3,434,665 | |
| IIY5000 | (14) 3,459,177 | |
| IIY5002 | (14) 3,464,930 | |
| IIY5004 | (14) 3,485,428 | |
| IIY5006 | (14) 3,497,036 | |
| IIY5007 | (14) 3,501,043 | |
| IIY14912 | (14) 3,538,861 | |
| IIY16123 | (14) 3,540,177 | |
| IIY5012 | (14) 3,544,909 | |
| IIY5014 | (14) 3,547,905 | |
| IIY5015 | (14) 3,557,072 | |
| IIY15836 | (14) 3,613,876 | |
| IIY5026 | (14) 3,700,742 | |
| IIY5027 | (14) 3,702,049 | |
| IIY14807 | (14) 3,772,678 | |
| IIY5031 | (14) 3,775,882 | |
| IIY5067 | (14) 4,196,012 | |
| IIY5071 | (14) 4,281,987 | |
| IIY5092 | (14) 4,496,833 | |
| IIY5093 | (14) 4,503,587 | |
| IIY5095 | (14) 4,505,241 | |
| IIY5096 | (14) 4,507,052 | |
| IIY16237 | (14) 38,646,206 | |

TABLE 1-continued

Listing of Markers (i.e. QTLs) that associate with SDS

| Marker Locus | Physical Map Position in Glyma 1.01 | Favorable Marker Allele |
|---|---|---|
| IIY5142 | (14) 47,132,559 | |
| IIY15626 | (15) 6,727,874 | |
| IIY5883 | (15) 6,944,188 | |
| IIY5900 | (15) 7,214,522 | |
| IIY6002 | (15) 9,681,005 | |
| SY3861 | (15) 9,860,854 | |
| IIY5358 | (15) 11,236,766 | |
| IIY5359 | (15) 11,416,165 | |
| IIY5360 | (15) 11,421,179 | |
| IIY5369 | (15) 12,225,369 | |
| IIY5370 | (15) 12,247,603 | |
| IIY5371 | (15) 12,296,765 | |
| IIY5373 | (15) 12,415,883 | |
| IIY5377 | (15) 12,459,252 | |
| IIY5381 | (15) 12,571,729 | |
| IIY5385 | (15) 12,636,016 | |
| IIY5397 | (15) 13,194,129 | |
| IIY5399 | (15) 13,201,666 | |
| IIY5400 | (15) 13,202,525 | |
| IIY5401 | (15) 13,246,726 | |
| IIY5402 | (15) 13,354,806 | |
| IIY5404 | (15) 13,361,773 | |
| IIY5405 | (15) 13,375,102 | |
| IIY5406 | (15) 13,379,361 | |
| IIY5416 | (15) 13,721,899 | |
| SY3845 | (15) 14,324,934 | |
| IIY5421 | (15) 14,326,320 | |
| IIY5424 | (15) 14,391,731 | |
| IIY5426 | (15) 14,474,786 | |
| IIY15658 | (15) 14,535,373 | |
| IIY6069 | (15) 14,876 | |
| IIY6528 | (16) 426,070 | |
| SY0860AQ | (16) 1,103,309 | |
| IIY6051 | (16) 1,316,187 | |
| IIY6545 | (16) 5,472,668 | |
| IIY6546 | (16) 5,490,552 | |
| IIY6549 | (16) 5,525,211 | |
| IIY6550 | (16) 5,531,626 | |
| IIY6551 | (16) 5,540,771 | |
| IIY6556 | (16) 5,636,183 | |
| IIY6580 | (16) 6,684,494 | |
| IIY6581 | (16) 6,685,999 | |
| IIY6582 | (16) 6,687,176 | |
| IIY6583 | (16) 6,708,276 | |
| IIY6584 | (16) 6,716,691 | |
| IIY15610 | (16) 7,421,321 | |
| IIY6033 | (16) 10,981,222 | |
| IIY16769 | (16) 24,683,329 | |
| SY1090A | (16) 26,959,365 | T |
| IIY6154 | (16) 27,561,001 | |
| IIY16361 | (16) 29,937,298 | |
| IIY6235 | (16) 31,012,050 | |
| SY3106 | (16) 31,114,052 | |
| SY0086A | (16) 31,075,727 | C |
| IIY6254 | (16) 31,189,225 | |
| IIY6255 | (16) 31,191,435 | |
| IIY6256 | (16) 31,204,451 | |
| IIY6257 | (16) 31,207,130 | |
| IIY6258 | (16) 31,211,000 | |
| IIY6259 | (16) 31,221,894 | |
| IIY6260 | (16) 31,223,475 | |
| IIY6262 | (16) 31,230,693 | |
| SY3107 | (16) 31,272,877 | |
| IIY6265 | (16) 31,273,194 | |
| IIY15656 | (16) 31,273,562 | |
| IIY6272 | (16) 31,450,016 | |
| IIY16517 | (16) 31,450,214 | |
| IIY6274 | (16) 31,472,725 | |
| IIY6276 | (16) 31,476,359 | |
| IIY6277 | (16) 31,477,475 | |
| IIY6279 | (16) 31,480,833 | |
| IIY6283 | (16) 31,574,435 | |
| IIY6289 | (16) 31,790,078 | |
| IIY6290 | (16) 31,792,317 | |
| SY3108 | (16) 31,860,682 | |
| SY3109 | (16) 31,861,195 | |
| SY3110 | (16) 31,863,327 | |
| SY0871A | (16) 31,869,001 | T |
| IIY6295 | (16) 31,952,066 | |
| IIY6296 | (16) 31,968,800 | |
| SY3111 | (16) 31,972,789 | |
| SY3004 | (16) 31,995,555 | |
| SY3112 | (16) 32,084,966 | |
| SY0096A | (16) 32,101,062 | T |
| SY3104 | (16) 32,105,028 | |
| IIY6302 | (16) 32,119,112 | |
| IIY6305 | (16) 32,154,287 | |
| IIY6306 | (16) 32,209,287 | |
| SY3119 | (16) 32,305,961 | |
| SY3113 | (16) 32,307,916 | |
| IIY6312 | (16) 32,313,679 | |
| SY3114 | (16) 32,474,449 | |
| IIY6322 | (16) 32,545,163 | |
| SY3105 | (16) 32,853,255 | |
| IIY15433 | (16) 32,864,315 | |
| SY0567A | (16) 32,881,385 | A |
| SY0098BQ | (16) 32,881,404 | C |
| SY0098B | (16) 32,881,452 | |
| SY3115 | (16) 32,896,631 | |
| IIY6329 | (16) 32,902,856 | |
| IIY15904 | (16) 32,903,366 | |
| IIY6331 | (16) 32,926,931 | |
| IIY6338 | (16) 33,192,063 | |
| SY3117 | (16) 33,435,467 | |
| IIY6369 | (16) 34,663,137 | |
| IIY6372 | (16) 34,672,088 | |
| IIY6386 | (16) 35,305,988 | |
| IIY6387 | (16) 35,315,590 | |
| IIY6388 | (16) 35,331,550 | |
| IIY6390 | (16) 35,409,880 | |
| IIY6391 | (16) 35,413,993 | |
| IIY6394 | (16) 35,430,549 | |
| IIY6404 | (16) 35,817,263 | |
| IIY6418 | (16) 36,127,976 | |
| IIY6451 | (16) 36,596,355 | |
| IIY6459 | (16) 36,657,770 | |
| IIY6493 | (16) 37,220,666 | |
| SY0346B | (17) 19,056,429 | T |
| IIY2778 | (18) 386,232 | |
| SY0992A | (18) 1,231,629 | A |
| SY0007AQ | (18) 1,736,100 | G |
| SY0007B | (18) 1,736,136 | G |
| IIY7360 | (18) 2,026,928 | |
| IIY7362 | (18) 2,031,641 | |
| IIY7363 | (18) 2,035,651 | |
| SY0445A | (18) 2,042,727 | T |
| IIY7380 | (18) 2,304,350 | |
| IIY7386 | (18) 2,351,813 | |
| SY1324A | (18) 2,833,147 | T |
| IIY7423 | (18) 2,899,312 | |
| IIY7476 | (18) 3,793,626 | |
| SY3864 | (18) 6,636,489 | |
| IIY7952 | (18) 6,639,997 | |
| IIY7953 | (18) 6,643,807 | |
| IIY7955 | (18) 6,775,997 | |
| HY16082 | (18) 6,823,886 | |
| IIY7960 | (18) 6,851,819 | |
| IIY8014 | (18) 7,898,429 | |
| IIY8046 | (18) 9,133,223 | |
| IIY7627 | (18) 56,055,793 | |
| IIY7628 | (18) 56,058,614 | |
| IIY7630 | (18) 56,083,805 | |
| SY0719A | (18) 56,086,233 | |
| IIY7632 | (18) 56,094,994 | |
| IIY449 | (18) 56,114,692 | |
| IIY7634 | (18) 56,131,550 | |
| IIY7635 | (18) 56,173,024 | |
| IIY7643 | (18) 56,340,319 | |
| IIY7645 | (18) 56,342,963 | |
| HY15456 | (18) 56,343,071 | |

TABLE 1-continued

Listing of Markers (i.e. QTLs) that associate with SDS

| Marker Locus | Physical Map Position in Glyma 1.01 | Favorable Marker Allele |
|---|---|---|
| IIY7649 | (18) 56,471,039 | |
| IIY7650 | (18) 56,474,480 | |
| IIY7651 | 56,476,885 | |
| IIY7674 | (18) 56,949,424 | |
| SY3865 | (18) 57,355,755 | |
| IIY7721 | (18) 57,493,910 | |
| IIY7722 | (18) 57,517,073 | |
| IIY7723 | (18) 57,520,772 | |
| IIY7725 | (18) 57,526,751 | |
| IIY16541 | (18) 57,531,829 | |
| IIY7727 | (18) 57,536,483 | |
| IIY7728 | (18) 57,538,074 | |
| IIY7730 | (18) 57,545,098 | |
| IIY7731 | (18) 57,551,138 | |
| IIY7732 | (18) 57,567,097 | |
| IIY7733 | (18) 57,569,675 | |
| IIY7734 | (18) 57,571,410 | |
| IIY7735 | (18) 57,575,579 | |
| IIY7736 | (18) 57,577,959 | |
| IIY7737 | (18) 57,582,307 | |
| IIY7738 | (18) 57,583,324 | |
| SY0975AQ | (18) 57,583,518 | |
| IIY7740 | (18) 57,633,573 | |
| IIY7742 | (18) 57,699,682 | |
| IIY7743 | (18) 57,705,434 | |
| IIY7745 | (18) 57,733,346 | |
| IIY7748 | (18) 57,748,381 | |
| SY1329AQ | (18) 57,781,968 | |
| IIY7749 | (18) 57,789,581 | |
| IIY7750 | (18) 57,798,727 | |
| IIY7752 | (18) 57,809,604 | |
| IIY7753 | (18) 57,811,692 | |
| IIY7754 | (18) 57,814,013 | |
| IIY7755 | (18) 57,823,718 | |
| IIY7756 | (18) 57,833,668 | |
| IIY7757 | (18) 57,834,595 | |
| IIY7758 | (18) 57,843,062 | |
| IIY7759 | (18) 57,849,866 | |
| SY3860 | (18) 61,139,088 | |
| IIY7934 | (18) 61,918,169 | |
| IIY7935 | (18) 61,920,237 | |
| IIY7936 | (18) 61,921,542 | |
| IIY8227 | (19) 37,032,286 | |
| SY0883AQ | (19) 37,996,663 | |
| IIY8248 | (19) 38,060,820 | |
| IIY8399 | (19) 43,931,738 | |
| SY1353AQ | (19) 44,566,829 | |
| SY0632A | (19) 48,091,800 | C |
| SY1003A | (19) 48,609,911 | T |
| SY0996AQ | (19) 48,638,208 | |
| IIY8544 | (19) 48,816,225 | |
| SY0635A | (19) 49,845,462 | G |
| SY0636A | (19) 50,222,617 | A |
| SY0984A | (19) 50,414,093 | C |
| SY0634B | (19) 50,424,620 | T |

TABLE 2

Is a list of genes that may be introduced into a plant's genome (i.e. either through plant introgression, transgenic expression or genome editing) to confer in said plant SDS resistance and/or tolerance. Physical position based on reference sequence Glyma 1.01.

| Annotation | Chromosomal Location | Location Start | Location Stop |
|---|---|---|---|
| 60S ribosomal protein L31 | Gm05 | 40,045,211 | 40,045,539 |
| 40S ribosomal protein S29 | Gm10 | 47,878,687 | 47,879,789 |
| 40S ribosomal protein S7 | Gm09 | 38,241,418 | 38,243,784 |
| Metal ion binding protein | Gm04 | 269,451 | 270,100 |
| Type 1 metallothionein | Gm17 | 38,851,860 | 38,853,036 |
| Metallothionein-like protein | Gm06 | 39,710,511 | 39,711,522 |
| Ribulose-1,5-bisphosphate carboxylase small subunit rbcS1 | Gm19 | 7,217,084 | 7,218,331 |
| Chloroplast thioredoxin M-type | Gm04 | 47,864,864 | 47,866,553 |
| Ferredoxin-2, chloroplast precursor | Gm08 | 9,778,931 | 9,779,808 |
| PSBP; photosystem II oxygen-evolving complex 23K protein | Gm18 | 60,969,634 | 60,973,182 |
| Sterol methyltransferase C-terminal | Gm10 | 11,893,875 | 11,894,558 |
| Serine hydroxymethyltransferase | Gm08 | 35,672,052 | 35,672,751 |
| S-adenosylmethionine synthetase, C-terminal domain | Gm15 | 20,280,340 | 20,281,144 |
| Gamma-glutamyl hydrolase | Gm13 | 35,908,480 | 35,910,086 |
| Glycine dehydrogenase | Gm14 | 9,009,817 | 9,011,444 |
| Carbonic anhydrase | Gm19 | 740,118 | 743,673 |
| Carbonic anhydrase | Gm15 | 4,421,551 | 4,425,381 |
| Photosystem I reaction center subunit N | Gm06 | 12,240,040 | 12,241,246 |
| Photosystem I reaction center subunit IV A | Gm10 | 3,737,191 | 3,742,989 |
| Chlorophyll A-B binding protein | Gm16 | 30,309,257 | 30,311,354 |
| Chlorophyll A-B binding protein 3 | Gm08 | 6,268,863 | 6,269,794 |
| Chlorophyll A-B binding protein | Gm02 | 51,103,849 | 51,104,828 |
| Chlorophyll A-B binding protein | Gm16 | 31,995,542 | 31,996,388 |
| Protein of unknown function DUF707 | Gm12 | 31,949,417 | 31,952,450 |
| Hypothetical protein | Gm13 | 6,663,529 | 6,669,763 |
| Proton gradient regulation 5 | Gm10 | 36,282,956 | 36,284,303 |
| Actin 5 | Gm12 | 4,647,695 | 4,648,610 |
| Senescence-associated protein DIN1 | Gm01 | 49,074,834 | 49,077,223 |
| Ribonucleoprotein | Gm10 | 5,369,913 | 5,371,337 |

In some embodiments, the marker allele(s) may be located in one or more of the chromosomal intervals as described in Table 1. For example a chromosomal interval may comprise:

1) the chromosomal interval defined by and including SY0302B and SY0303A;
2) the chromosomal interval defined by and including SY0060A and SY0906A;
3) the chromosomal interval defined by and including SY0946A and SY1005A;
4) the chromosomal interval defined by and including SY0946A and SY0916A;
5) the chromosomal interval defined by and including SY0916A and SY1005A;
6) the chromosomal interval defined by and including SY1032A and SY0421A;
7) the chromosomal interval defined by and including SY1032A and SY0132A;
8) the chromosomal interval defined by and including SY1032A and SY0422A;
9) the chromosomal interval defined by and including SY1032A and SY0080A;
10) the chromosomal interval defined by and including SY0132A and SY0421A;
11) the chromosomal interval defined by and including SY0132A and SY0422A;
12) the chromosomal interval defined by and including SY0132A and SY0080A;
13) the chromosomal interval defined by and including SY0422A and SY0421A;

14) the chromosomal interval defined by and including SY0422A and SY0080A;
15) the chromosomal interval defined by and including SY0080A and SY0421A;
16) the chromosomal interval defined by and including SY0118B and SY0126C;
17) the chromosomal interval defined by and including SY0118B and SY0121A;
18) the chromosomal interval defined by and including SY0118B and SY0125B;
19) the chromosomal interval defined by and including SY0121A and SY0126C;
20) the chromosomal interval defined by and including SY0121A and SY0125B;
21) the chromosomal interval defined by and including SY0125B and SY0126C;
22) the chromosomal interval defined by and including SY1090A and SY0098B;
23) the chromosomal interval defined by and including SY1090A and SY0871A;
24) the chromosomal interval defined by and including SY1090A and SY0096A;
25) the chromosomal interval defined by and including SY1090A and SY0567A;
26) the chromosomal interval defined by and including SY0871A and SY0098B;
27) the chromosomal interval defined by and including SY0871A and SY0096A;
28) the chromosomal interval defined by and including SY0871A and SY0567A;
29) the chromosomal interval defined by and including SY0096A and SY0098B;
30) the chromosomal interval defined by and including SY0096A and SY0567A;
31) the chromosomal interval defined by and including SY0567A and SY0098B;
32) the chromosomal interval defined by and including SY0992A and SY1324A;
33) the chromosomal interval defined by and including SY0992A and SY0007A;
34) the chromosomal interval defined by and including SY0992A and SY0007B;
35) the chromosomal interval defined by and including SY0992A and SY0445A;
36) the chromosomal interval defined by and including SY0007A and SY1324A;
37) the chromosomal interval defined by and including SY0007A and SY0007B;
38) the chromosomal interval defined by and including SY0007A and SY0445A;
39) the chromosomal interval defined by and including SY0007B and SY1324A;
40) the chromosomal interval defined by and including SY0007B and SY0445A;
41) the chromosomal interval defined by and including SY0445A and SY1324A;
42) the chromosomal interval defined by and including SY0632A and SY0634B;
43) the chromosomal interval defined by and including SY0632A and SY1003A;
44) the chromosomal interval defined by and including SY0632A and SY0635A;
45) the chromosomal interval defined by and including SY0632A and SY0636A;
46) the chromosomal interval defined by and including SY0632A and SY0984A;
47) the chromosomal interval defined by and including SY1003A and SY0634B;
48) the chromosomal interval defined by and including SY1003A and SY0635A;
49) the chromosomal interval defined by and including SY1003A and SY0636A;
50) the chromosomal interval defined by and including SY1003A and SY0984A;
51) the chromosomal interval defined by and including SY0635A and SY0634B;
52) the chromosomal interval defined by and including SY0635A and SY0636A;
53) the chromosomal interval defined by and including SY0635A and SY0984A;
54) the chromosomal interval defined by and including SY0636A and SY0634B;
55) the chromosomal interval defined by and including SY0636A and SY0984A; and
56) the chromosomal interval defined by and including SY0984A and SY0634B, as well as any combination of (1)-(56) above.

In some embodiments, the marker may comprise marker alleles located in at least two different chromosomal intervals. For example, the marker may comprise one or more alleles located in the chromosomal interval defined by and including SY0007A and SY1324A and one or more alleles located in the chromosomal interval defined by and including SY0871A and SY0098B.

In some embodiments, the marker allele(s) may be located in one or more of the following chromosomal intervals as described in Table 1:
1) the chromosomal interval defined by and including a C allele at SY0302B and a T allele at SY0303A;
2) the chromosomal interval defined by and including a G allele at SY0060A and a C allele at SY0906A;
3) the chromosomal interval defined by and including an A allele at SY0060A and a C allele at SY0906A;
4) the chromosomal interval defined by and including a T allele at SY0946A and a T allele at SY1005A;
5) the chromosomal interval defined by and including a T allele at SY0946A and a T allele at SY0916A;
6) the chromosomal interval defined by and including a T allele at SY0916A and a T allele at SY1005A;
7) the chromosomal interval defined by and including an A allele at SY1032A and an insertion at SY0421A;
8) the chromosomal interval defined by and including an A allele at SY1032A and a T allele at SY0132A;
9) the chromosomal interval defined by and including an A allele at SY1032A and a C allele at SY0422A;
10) the chromosomal interval defined by and including an A allele at SY1032A and a T allele at SY0080A;
11) the chromosomal interval defined by and including a T allele at SY0132A and an insertion at SY0421A;
12) the chromosomal interval defined by and including a T allele at SY0132A and a C allele at SY0422A;
13) the chromosomal interval defined by and including a T allele at SY0132A and a T allele at SY0080A;
14) the chromosomal interval defined by and including a C allele at SY0422A and an insertion at SY0421A;
15) the chromosomal interval defined by and including a C allele at SY0422A and a T allele at SY0080A;
16) the chromosomal interval defined by and including a T allele at SY0080A and an insertion at SY0421A;
17) the chromosomal interval defined by and including a C allele at SY0118B and an A allele at SY0126C;
18) the chromosomal interval defined by and including a C allele at SY0118B and a C allele at SY0121A;

19) the chromosomal interval defined by and including a C allele at SY0118B and a G allele at SY0125B;
20) the chromosomal interval defined by and including a C allele at SY0121A and an A allele at SY0126C;
21) the chromosomal interval defined by and including a C allele at SY0121A and a G allele at SY0125B;
22) the chromosomal interval defined by and including a G allele at SY0125B and an A allele at SY0126C;
23) the chromosomal interval defined by and including a T allele at SY1090A and a C allele at SY0098B;
24) the chromosomal interval defined by and including a T allele at SY1090A and a T allele at SY0098B;
25) the chromosomal interval defined by and including a T allele at SY1090A and an A allele at SY0871A;
26) the chromosomal interval defined by and including a T allele at SY1090A and an T allele at SY0871A;
27) the chromosomal interval defined by and including a T allele at SY1090A and a T allele at SY0096A;
28) the chromosomal interval defined by and including a T allele at SY1090A and a C allele at SY0096A;
29) the chromosomal interval defined by and including a T allele at SY1090A and an A allele at SY0567A;
30) the chromosomal interval defined by and including a T allele at SY1090A and an T allele at SY0567A;
31) the chromosomal interval defined by and including an A allele at SY0871A and a C allele at SY0098B;
32) the chromosomal interval defined by and including an A allele at SY0871A and a T allele at SY0098B;
33) the chromosomal interval defined by and including an A allele at SY0871A and a T allele at SY0096A;
34) the chromosomal interval defined by and including an A allele at SY0871A and a C allele at SY0096A;
35) the chromosomal interval defined by and including an A allele at SY0871A and an A allele at SY0567A;
36) the chromosomal interval defined by and including an A allele at SY0871A and a T allele at SY0567A;
37) the chromosomal interval defined by and including a T allele at SY0871A and a C allele at SY0098B;
38) the chromosomal interval defined by and including a T allele at SY0871A and a T allele at SY0098B;
39) the chromosomal interval defined by and including a T allele at SY0871A and a T allele at SY0096A;
40) the chromosomal interval defined by and including a T allele at SY0871A and a C allele at SY0096A;
41) the chromosomal interval defined by and including a T allele at SY0871A and an A allele at SY0567A;
42) the chromosomal interval defined by and including a T allele at SY0871A and a T allele at SY0567A;
43) the chromosomal interval defined by and including a T allele at SY0096A and a C allele at SY0098B;
44) the chromosomal interval defined by and including a T allele at SY0096A and a T allele at SY0098B;
45) the chromosomal interval defined by and including a T allele at SY0096A and an A allele at SY0567A;
46) the chromosomal interval defined by and including a T allele at SY0096A and a T allele at SY0567A;
47) the chromosomal interval defined by and including a C allele at SY0096A and a C allele at SY0098B;
48) the chromosomal interval defined by and including a C allele at SY0096A and a T allele at SY0098B;
49) the chromosomal interval defined by and including a C allele at SY0096A and an A allele at SY0567A;
50) the chromosomal interval defined by and including a C allele at SY0096A and a T allele at SY0567A;
51) the chromosomal interval defined by and including an A allele at SY0567A and a C allele at SY0098B;
52) the chromosomal interval defined by and including an A allele at SY0567A and a T allele at SY0098B;
53) the chromosomal interval defined by and including a T allele at SY0567A and a C allele at SY0098B;
54) the chromosomal interval defined by and including a T allele at SY0567A and a T allele at SY0098B;
55) the chromosomal interval defined by and including an A allele at SY0992A and a T allele at SY1324A;
56) the chromosomal interval defined by and including an A allele at SY0992A and a G allele at SY0007A;
57) the chromosomal interval defined by and including an A allele at SY0992A and a T allele at SY0007A;
58) the chromosomal interval defined by and including an A allele at SY0992A and a G allele at SY0007B;
59) the chromosomal interval defined by and including an A allele at SY0992A and a T allele at SY0445A;
60) the chromosomal interval defined by and including a C allele at SY0992A and a T allele at SY1324A;
61) the chromosomal interval defined by and including a C allele at SY0992A and a G allele at SY0007A;
62) the chromosomal interval defined by and including a C allele at SY0992A and a T allele at SY0007A;
63) the chromosomal interval defined by and including a C allele at SY0992A and a G allele at SY0007B;
64) the chromosomal interval defined by and including a C allele at SY0992A and a T allele at SY0445A;
65) the chromosomal interval defined by and including a G allele at SY0007A and a T allele at SY1324A;
66) the chromosomal interval defined by and including a G allele at SY0007A and a G allele at SY0007B;
67) the chromosomal interval defined by and including a G allele at SY0007A and a T allele at SY0445A;
68) the chromosomal interval defined by and including a T allele at SY0007A and a T allele at SY1324A;
69) the chromosomal interval defined by and including a T allele at SY0007A and a G allele at SY0007B;
70) the chromosomal interval defined by and including a T allele at SY0007A and a T allele at SY0445A;
71) the chromosomal interval defined by and including a G allele at SY0007B and a T allele at SY1324A;
72) the chromosomal interval defined by and including a G allele at SY0007B and a T allele at SY0445A;
73) the chromosomal interval defined by and including a T allele at SY0445A and a T allele at SY1324A;
74) the chromosomal interval defined by and including a C allele at SY0632A and a T allele at SY0634B;
75) the chromosomal interval defined by and including a C allele at SY0632A and a T allele at SY1003A;
76) the chromosomal interval defined by and including a C allele at SY0632A and a G allele at SY0635A;
77) the chromosomal interval defined by and including a C allele at SY0632A and an A allele at SY0636A;
78) the chromosomal interval defined by and including a C allele at SY0632A and a C allele at SY0984A;
79) the chromosomal interval defined by and including a T allele at SY1003A and a T allele at SY0634B;
80) the chromosomal interval defined by and including a T allele at SY1003A and a G allele at SY0635A;
81) the chromosomal interval defined by and including a T allele at SY1003A and an A allele at SY0636A;
82) the chromosomal interval defined by and including a T allele at SY1003A and a C allele at SY0984A;
83) the chromosomal interval defined by and including a G allele at SY0635A and a T allele at SY0634B;
84) the chromosomal interval defined by and including a G allele at SY0635A and an A allele at SY0636A;

85) the chromosomal interval defined by and including a G allele at SY0635A and a C allele at SY0984A;
86) the chromosomal interval defined by and including an A allele at SY0636A and a T allele at SY0634B;
87) the chromosomal interval defined by and including an A allele at SY0636A and a C allele at SY0984A; and
88) the chromosomal interval defined by and including a C allele at SY0984A and a T allele at SY0634B,
as well as any combination of (1)-(88) above.

In some embodiments, the marker may comprise marker alleles located in at least two different chromosomal intervals. For example, the marker may comprise one or more alleles located in the chromosomal interval defined by and including a G allele or a T allele at SY0007A and a T allele SY1324A and one or more alleles located in the chromosomal interval defined by and including an A allele or a T allele at SY0871A and a T allele or a C allele at SY0098B.

In some embodiments, the marker may comprise, consist essentially of or consist of one or more than one of the following alleles as described in Table 1:
1) a C allele at SY0302B;
2) a T allele at SY0303A;
3) a G allele or an A allele at SY0060A;
4) a C allele at SY0906A;
5) a T allele at SY0946A;
6) a T allele at SY0916A;
7) a T allele at SY1005A;
8) an A allele at SY1032A;
9) a T allele at SY0132A;
10) a C allele at SY0422A;
11) a T allele at SY0080A;
12) an insertion at SY0421A;
13) a C allele at SY0118B;
14) a C allele at SY0121A;
15) a G allele at SY0125B;
16) an A allele at SY0126C;
17) a T allele at SY1090A;
18) an A allele or a T allele at SY0871A;
19) a T allele or a C allele at SY0096A;
20) an A allele or a T allele at SY0567A;
21) a C allele or a T allele at SY0098B;
22) a T allele at SY0346B;
23) an A allele or a C allele at SY0992A;
24) a G allele or a T allele at SY0007A;
25) a G allele at SY0007B;
26) a T allele at SY0445A;
27) a T allele at SY1324A;
28) a C allele at SY0632A;
29) a T allele at SY1003A;
30) a G allele at SY0635A;
31) an A allele at SY0636A;
32) a C allele at SY0984A;
33) a T allele at SY0634B; and
34) any combination of (1)-(33) above.

In some embodiments, the marker may comprise, consist essentially of or consist of one or more of the following alleles as described in Table 1:
1) a T allele at SY0303A;
2) a C allele at SY0906A;
3) a T allele at SY0946A;
4) a T allele at SY0080A;
5) a C allele at SY0121A;
6) a C or a T allele at SY0098B;
7) a T allele at SY0346B;
8) a G or a T allele at SY0007A;
9) a C allele at SY0984A; and
10) any combination of (1)-(9) above.

In some embodiments, the marker may comprise, consist essentially of or consist of any marker linked to one or more of the aforementioned markers. That is, any allele and/or haplotype that is in linkage disequilibrium with any of the aforementioned markers may also be used to identify, select and/or produce a soybean plant with enhanced SDS tolerance. Linked markers may be determined, for example, by using resources available on the SoyBase website (http://soybase.org) or the U.S. Department of Energy Joint Genome Institute's soybean website (http://genome.jgi-psforg/soybean/soybean.home.html).

In some embodiments, the marker may comprise, consist essentially of or consist of any marker allele(s) located within about 10 cM of any one of the aforementioned markers. For example, the marker may comprise, consist essentially of or consist of one or more marker alleles located within about 10 cM of SY0303A, SY0906A, SY0946A, SY0080A, SY0121A, SY0098B, SY0346B, SY0007A or SY0984A.

Marker-Assisted Selection

Markers can be used in a variety of plant breeding applications. See, e.g., Staub et al., *Hortscience* 31: 729 (1996); Tanksley, *Plant Molecular Biology Reporter* 1: 3 (1983). One of the main areas of interest is to increase the efficiency of backcrossing and introgressing genes using marker-assisted selection (MAS). In general, MAS takes advantage of genetic markers that have been identified as having a significant likelihood of co-segregation with a desired trait. Such markers are presumed to be in/near the gene(s) that give rise to the desired phenotype, and their presence indicates that the plant will possess the desired trait. Plants which possess the marker are expected to transfer the desired phenotype to their progeny.

A marker that demonstrates linkage with a locus affecting a desired phenotypic trait provides a useful tool for the selection of the trait in a plant population. This is particularly true where the phenotype is hard to assay or occurs at a late stage in plant development.

Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing or imparting the trait. Having flanking markers decreases the chances that false positive selection will occur. The ideal situation is to have a marker in the gene itself, so that recombination cannot occur between the marker and the gene. Such a marker is called a "perfect marker."

When a gene is introgressed by MAS, it is not only the gene that is introduced but also the flanking regions. Gepts, *Crop Sci* 42:1780 (2002). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite soybean line. This is also sometimes referred to as "yield drag." The size of the flanking region can be decreased by additional backcrossing, although this is not always successful, as breeders do not have control over the size of the region or the recombination breakpoints. Young et al., *Genetics* 120:579 (1998). In classical breeding, it is usually only by chance that recombinations that contribute to a reduction in the size of the donor segment are selected. Tanksley et al., *Biotechnology* 7: 257 (1989). Even after 20 backcrosses, one might find a sizeable piece of the donor chromosome still linked to the gene being selected. With markers, however, it is possible to select those rare individuals that have experienced recombination near the gene of interest. In 150 backcross plants, there is a 95% chance that at least one plant will have experienced a crossover within 1 cM of the gene, based on a single meiosis map distance. Markers allow for unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers. See Tanksley et al., supra. When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the soybean genome containing increasing densities of public soybean markers has facilitated soybean genetic mapping and MAS.

Of all the molecular marker types, SNPs are the most abundant and have the potential to provide the highest genetic map resolution. Bhattramakki et al., *Plant Molec. Biol.* 48:539 (2002). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants*, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

A number of SNP alleles together within a sequence, or across linked sequences, can be used to describe a haplotype for any particular genotype. Ching et al., *BMC Genet.* 3:19 (2002); Gupta et al., (2001), Rafalski, *Plant Sci.* 162:329 (2002b). Haplotypes can be more informative than single SNPs and can be more descriptive of any particular genotype. For example, a single SNP may be allele "T" for a specific SDS tolerant line or variety, but the allele "T" might also occur in the soybean breeding population being utilized for recurrent parents. In this case, a combination of alleles at linked SNPs may be more informative. Once a unique haplotype has been assigned to a donor chromosomal region, that haplotype can be used in that population or any subset thereof to determine whether an individual has a particular gene. The use of automated high throughput marker detection platforms known to those of ordinary skill in the art makes this process highly efficient and effective.

The markers of the present invention can be used in marker-assisted selection protocols to identify and/or select progeny with enhanced SDS tolerance. Such methods can comprise, consist essentially of or consist of crossing a first soybean plant or germplasm with a second soybean plant or germplasm, wherein the first soybean plant or germplasm comprises a marker associated with enhanced SDS tolerance, and selecting a progeny plant that possesses the marker. Either of the first and second soybean plants, or both, may be of a non-naturally occurring variety of soybean. In some embodiments, the second soybean plant or germplasm is of an elite variety of soybean. In some embodiments, the genome of the second soybean plant or germplasm is at least about 50%, 55%, 60%, 65%, 70%, 75%, 80%, 85%, 90%, 95%, 97%, 99% or 100% identical to that of an elite variety of soybean.

Methods for identifying and/or selecting an SDS tolerant soybean plant or germplasm may comprise, consist essentially of or consist of detecting the presence of a marker associated with enhanced SDS tolerance. The marker may be detected in any sample taken from the plant or germplasm, including, but not limited to, the whole plant or germplasm, a portion of said plant or germplasm (e.g., a seed chip, a leaf punch disk or a cell from said plant or germplasm) or a nucleotide sequence from said plant or germplasm. Such a sample may be taken from the plant or germplasm using any present or future method known in the art, including, but not limited to, automated methods of removing a portion of endosperm with a sharp blade, drilling a small hole in the seed and collecting the resultant powder, cutting the seed with a laser and punching a leaf disk. The soybean plant may be of a non-naturally occurring variety of soybean. In some embodiments, the genome of the soybean plant or germplasm is at least about 50%, 55%, 60%, 65%, 70%, 75%, 80%, 85%, 90%, 95%, 97%, 99% or 100% identical to that of an elite variety of soybean.

In some embodiments, the marker detected in the sample may comprise, consist essentially of or consist of one or more marker alleles located within a chromosomal interval selected from the group consisting of:

1) the chromosomal interval defined by and including a C allele at SY0302B and a T allele at SY0303A;
2) the chromosomal interval defined by and including a G allele or an A allele at SY0060A and a C allele at SY0906A;
3) the chromosomal interval defined by and including a T allele at SY0946A and a T allele at SY1005A;
4) the chromosomal interval defined by and including an A allele or a T allele at SY1032A and an insertion at SY0421A;
5) the chromosomal interval defined by and including a C allele at SY0118B and an A allele at SY0126C;
6) the chromosomal interval defined by and including T allele at SY1090A and a C allele or a T allele at SY0098B;
7) the chromosomal interval defined by and including an A allele or a C allele at SY00992A and a T allele at SY1324A;
8) the chromosomal interval defined by and including a C allele at SY0632A and a T allele at SY0634B; and
9) any combination of (1)-(8) above.

In some embodiments, the marker detected in the sample may comprise, consist essentially of or consist of one or more marker alleles selected from the group consisting of:

1) a C allele at SY0302B;
2) a T allele at SY0303A;
3) a G allele or an A allele at SY0060A;
4) a C allele at SY0906A;
5) a T allele at SY0946A;
6) a T allele at SY0916A;
7) a T allele at SY1005A;
8) an A allele at SY1032A;
9) a T allele at SY0132A;
10) a C allele at SY0422A;
11) a T allele at SY0080A;
12) an insertion at SY0421A;
13) a C allele at SY0118B;
14) a C allele at SY0121A;
15) a G allele at SY0125B;
16) an A allele at SY0126C;
17) a T allele at SY1090A;
18) an A allele or a T allele at SY0871A;
19) a T allele or a C allele at SY0096A;
20) an A allele or a T allele at SY0567A;
21) a C allele or a T allele at SY0098B;
22) a T allele at SY0346B;
23) an A allele or a C allele at SY0992A;
24) a G allele or a T allele at SY0007A;
25) a G allele at SY0007B;
26) a T allele at SY0445A;
27) a T allele at SY1324A;
28) a C allele at SY0632A;
29) a T allele at SY1003A;
30) a G allele at SY0635A;
31) an A allele at SY0636A;
32) a C allele at SY0984A;
33) a T allele at SY0634B; and
34) any combination of (1) through (33) above.

In some embodiments, the marker detected in the sample may comprise, consist essentially of or consist of one or more marker alleles selected from the group consisting of:
1) a T allele at SY0303A;
2) a C allele at SY0906A;
3) a T allele at SY0946A;
4) a T allele at SY0080A;
5) a C allele at SY0121A;
6) a C allele or a T allele at SY0098B;
7) a T allele at SY0346B;
8) a G allele or a T allele at SY0007A;
9) a C allele at SY0984A; and
10) any combination of (1) through (9) above.

Methods for producing an SDS tolerant soybean plant may comprise, consist essentially of or consist of detecting, in a germplasm, a marker associated with enhanced SDS tolerance and producing a soybean plant from said germplasm. The marker may be detected in any sample taken from the germplasm, including, but not limited to, a portion of said germplasm (e.g., a seed chip or a cell from said germplasm) or a nucleotide sequence from said germplasm. Such a sample may be taken from the germplasm using any present or future method known in the art, including, but not limited to, automated methods of removing a portion of endosperm with a sharp blade, drilling a small hole in the seed and collecting the resultant powder, cutting the seed with a laser and punching a leaf disk. The germplasm may be of a non-naturally occurring variety of soybean. In some embodiments, the genome of the germplasm is at least about 50%, 55%, 60%, 65%, 70%, 75%, 80%, 85%, 90%, 95%, 97%, 99% or 100% identical to that of an elite variety of soybean. An SDS tolerant soybean plant is then produced from the germplasm identified as having the marker associated with enhanced SDS tolerance according to methods well known in the art for breeding and producing plants from germplasm.

In some embodiments the markers listed in Table 1 may be combined with fungicides such as, but not limited to foliar fungicides (e.g. fluoxastrobin strobilurin and flutrialfol triazole) or seed treatments (e.g. fluopyram).

In some embodiments, the marker detected in the germplasm may comprise, consist essentially of or consist of one or more marker alleles located within a chromosomal interval selected from the group consisting of:
1) the chromosomal interval defined by and including a C allele at SY0302B and a T allele at SY0303A;
2) the chromosomal interval defined by and including a G allele or an A allele at SY0060A and a C allele at SY0906A;
3) the chromosomal interval defined by and including a T allele at SY0946A and a T allele at SY1005A;
4) the chromosomal interval defined by and including an A allele or a T allele at SY1032A and an insertion at SY0421A;
5) the chromosomal interval defined by and including a C allele at SY0118B and an A allele at SY0126C;
6) the chromosomal interval defined by and including T allele at SY1090A and a C allele or a T allele at SY0098B;
7) the chromosomal interval defined by and including an A allele or a C allele at SY00992A and a T allele at SY1324A;
8) the chromosomal interval defined by and including a C allele at SY0632A and a T allele at SY0634B; and
9) any combination of (1)-(17) above.

In some embodiments, the marker detected in the germplasm may comprise, consist essentially of or consist of one or more marker alleles selected from the group consisting of:
1) a C allele at SY0302B;
2) a T allele at SY0303A;
3) a G allele or an A allele at SY0060A;
4) a C allele at SY0906A;
5) a T allele at SY0946A;
6) a T allele at SY0916A;
7) a T allele at SY1005A;
8) an A allele at SY1032A;
9) a T allele at SY0132A;
10) a C allele at SY0422A;
11) a T allele at SY0080A;
12) an insertion at SY0421A;
13) a C allele at SY0118B;
14) a C allele at SY0121A;
15) a G allele at SY0125B;
16) an A allele at SY0126C;
17) a T allele at SY1090A;
18) an A allele or a T allele at SY0871A;
19) a T allele or a C allele at SY0096A;
20) an A allele or a T allele at SY0567A;
21) a C allele or a T allele at SY0098B;
22) a T allele at SY0346B;
23) an A allele or a C allele at SY0992A;
24) a G allele or a T allele at SY0007A;
25) a G allele at SY0007B;
26) a T allele at SY0445A;
27) a T allele at SY1324A;
28) a C allele at SY0632A;
29) a T allele at SY1003A;
30) a G allele at SY0635A;
31) an A allele at SY0636A;
32) a C allele at SY0984A;

33) a T allele at SY0634B; and
34) any combination of (1) through (33) above.

In some embodiments, the marker detected in the germplasm may comprise, consist essentially of or consist of one or more marker alleles selected from the group consisting of:
1) a T allele at SY0303A;
2) a C allele at SY0906A;
3) a T allele at SY0946A;
4) a T allele at SY0080A;
5) a C allele at SY0121A;
6) a C allele or a T allele at SY0098B;
7) a T allele at SY0346B;
8) a G allele or a T allele at SY0007A;
9) a C allele at SY0984A; and
10) any combination of (1) through (9) above.

Methods for producing and/or selecting an SDS tolerant soybean plant or germplasm may comprise crossing a first soybean plant or germplasm with a second soybean plant or germplasm, wherein said first soybean plant or germplasm comprises a marker associated with enhanced SDS tolerance, and selecting a progeny plant or germplasm comprising said marker associated with enhanced SDS tolerance. Either the first or second soybean plant or germplasm, or both, may be of a non-naturally occurring variety of soybean. In some embodiments, the second soybean plant or germplasm is of an elite variety of soybean. In some embodiments, the genome of the second soybean plant or germplasm is at least about 50%, 55%, 60%, 65%, 70%, 75%, 80%, 85%, 90%, 95%, 97%, 99% or 100% identical to that of an elite variety of soybean.

In some embodiments, the marker may comprise, consist essentially of or consist of one or more marker alleles located within a chromosomal interval selected from the group consisting of:
1) the chromosomal interval defined by and including a C allele at SY0302B and a T allele at SY0303A;
2) the chromosomal interval defined by and including a G allele or an A allele at SY0060A and a C allele at SY0906A;
3) the chromosomal interval defined by and including a T allele at SY0946A and a T allele at SY1005A;
4) the chromosomal interval defined by and including an A allele or a T allele at SY1032A and an insertion at SY0421A;
5) the chromosomal interval defined by and including a C allele at SY0118B and an A allele at SY0126C;
6) the chromosomal interval defined by and including T allele at SY1090A and a C allele or a T allele at SY0098B;
7) the chromosomal interval defined by and including an A allele or a C allele at SY00992A and a T allele at SY1324A;
8) the chromosomal interval defined by and including a C allele at SY0632A and a T allele at SY0634B; and
9) any combination of (1)-(8) above.

In some embodiments, the marker may comprise, consist essentially of or consist of one or more marker alleles selected from the group consisting of:
1) a C allele at SY0302B;
2) a T allele at SY0303A;
3) a G allele or an A allele at SY0060A;
4) a C allele at SY0906A;
5) a T allele at SY0946A;
6) a T allele at SY0916A;
7) a T allele at SY1005A;
8) an A allele at SY1032A;
9) a T allele at SY0132A;
10) a C allele at SY0422A;
11) a T allele at SY0080A;
12) an insertion at SY0421A;
13) a C allele at SY0118B;
14) a C allele at SY0121A;
15) a G allele at SY0125B;
16) an A allele at SY0126C;
17) a T allele at SY1090A;
18) an A allele or a T allele at SY0871A;
19) a T allele or a C allele at SY0096A;
20) an A allele or a T allele at SY0567A;
21) a C allele or a T allele at SY0098B;
22) a T allele at SY0346B;
23) an A allele or a C allele at SY0992A;
24) a G allele or a T allele at SY0007A;
25) a G allele at SY0007B;
26) a T allele at SY0445A;
27) a T allele at SY1324A;
28) a C allele at SY0632A;
29) a T allele at SY1003A;
30) a G allele at SY0635A;
31) an A allele at SY0636A;
32) a C allele at SY0984A;
33) a T allele at SY0634B; and
34) any combination of (1) through (33) above.

In some embodiments, the marker may comprise, consist essentially of or consist of one or more marker alleles selected from the group consisting of:
1) a T allele at SY0303A;
2) a C allele at SY0906A;
3) a T allele at SY0946A;
4) a T allele at SY0080A;
5) a C allele at SY0121A;
6) a C allele or a T allele at SY0098B;
7) a T allele at SY0346B;
8) a G allele or a T allele at SY0007A;
9) a C allele at SY0984A; and
10) any combination of (1) through (9) above.

Also provided herein is a method of introgressing an allele associated with enhanced SDS tolerance into a soybean plant. Such methods for introgressing an allele associated with enhanced SDS tolerance into a soybean plant or germplasm may comprise, consist essentially of or consist of crossing a first soybean plant or germplasm comprising said allele (the donor) with a second soybean plant or germplasm that lacks said allele (the recurrent parent) and repeatedly backcrossing progeny comprising said allele with the recurrent parent. Progeny comprising said allele may be identified by detecting, in their genomes, the presence of a marker associated with enhanced SDS tolerance. The marker may be detected in any sample taken from the progeny, including, but not limited to, a portion of said progeny (e.g., a seed chip, a leaf punch disk or a cell from said plant or germplasm) or a nucleotide sequence from said progeny. Such a sample may be taken from the progeny using any present or future method known in the art, including, but not limited to, automated methods of removing a portion of endosperm with a sharp blade, drilling a small hole in the seed and collecting the resultant powder, cutting the seed with a laser and punching a leaf disk. Either the donor or the recurrent parent, or both, may be of a non-naturally occurring variety of soybean. In some embodiments, the recurrent parent is of an elite variety of soybean. In some embodiments, the genome of the recurrent parent is at least about 50%, 55%, 60%, 65%, 70%, 75%, 80%, 85%, 90%, 95%, 97%, 99% or 100% identical to that of an elite variety of soybean.

In some embodiments, the marker used to identify progeny comprising an allele associated with enhanced SDS tolerance may comprise, consist essentially of or consist of one or more marker alleles located within a chromosomal interval selected from the group consisting of:
1) the chromosomal interval defined by and including a C allele at SY0302B and a T allele at SY0303A;
2) the chromosomal interval defined by and including a G allele or an A allele at SY0060A and a C allele at SY0906A;
3) the chromosomal interval defined by and including a T allele at SY0946A and a T allele at SY1005A;
4) the chromosomal interval defined by and including an A allele or a T allele at SY1032A and an insertion at SY0421A;
5) the chromosomal interval defined by and including a C allele at SY0118B and an A allele at SY0126C;
6) the chromosomal interval defined by and including T allele at SY1090A and a C allele or a T allele at SY0098B;
7) the chromosomal interval defined by and including an A allele or a C allele at SY00992A and a T allele at SY1324A;
8) the chromosomal interval defined by and including a C allele at SY0632A and a T allele at SY0634B; and
9) any combination of (1)-(8) above.

In some embodiments, the marker may comprise, consist essentially of or consist of marker alleles located in at least two different chromosomal intervals. For example, the marker may comprise one or more alleles located in the chromosomal interval defined by and including SY0007A and SY1324A and one or more alleles located in the chromosomal interval defined by and including SY0871A and SY0098B.

In some embodiments, the marker used to identify progeny comprising an allele associated with enhanced SDS tolerance may comprise, consist essentially of or consist of one or more marker alleles selected from the group consisting of:
1) a C allele at SY0302B;
2) a T allele at SY0303A;
3) a G allele or an A allele at SY0060A;
4) a C allele at SY0906A;
5) a T allele at SY0946A;
6) a T allele at SY0916A;
7) a T allele at SY1005A;
8) an A allele at SY1032A;
9) a T allele at SY0132A;
10) a C allele at SY0422A;
11) a T allele at SY0080A;
12) an insertion at SY0421A;
13) a C allele at SY0118B;
14) a C allele at SY0121A;
15) a G allele at SY0125B;
16) an A allele at SY0126C;
17) a T allele at SY1090A;
18) an A allele or a T allele at SY0871A;
19) a T allele or a C allele at SY0096A;
20) an A allele or a T allele at SY0567A;
21) a C allele or a T allele at SY0098B;
22) a T allele at SY0346B;
23) an A allele or a C allele at SY0992A;
24) a G allele or a T allele at SY0007A;
25) a G allele at SY0007B;
26) a T allele at SY0445A;
27) a T allele at SY1324A;
28) a C allele at SY0632A;
29) a T allele at SY1003A;
30) a G allele at SY0635A;
31) an A allele at SY0636A;
32) a C allele at SY0984A;
33) a T allele at SY0634B; and
34) any combination of (1) through (33) above.

In some embodiments, the marker used to identify progeny comprising an allele associated with enhanced SDS tolerance may comprise, consist essentially of or consist of one or more marker alleles selected from the group consisting of:
1) a T allele at SY0303A;
2) a C allele at SY0906A;
3) a T allele at SY0946A;
4) a T allele at SY0080A;
5) a C allele at SY0121A;
6) a C allele or a T allele at SY0098B;
7) a T allele at SY0346B;
8) a G allele or a T allele at SY0007A;
9) a C allele at SY0984A; and
10) any combination of (1) through (9) above.

SDS Tolerant Soybean Plants and Germplasms

The present invention provides SDS tolerant soybean plants and germplasms. As discussed above, the methods of the present invention may be utilized to identify, produce and/or select an SDS tolerant soybean plant or germplasm. In addition to the methods described above, an SDS tolerant soybean plant or germplasm may be produced by any method whereby a marker associated with enhanced SDS tolerance is introduced into the soybean plant or germplasm, including, but not limited to, transformation, protoplast transformation or fusion, a double haploid technique, embryo rescue, and/or by any other nucleic acid transfer system.

In some embodiments, the soybean plant or germplasm comprises a non-naturally occurring variety of soybean. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The SDS tolerant soybean plant or germplasm may be the progeny of a cross between an elite variety of soybean and a variety of soybean that comprises an allele associated with enhanced SDS tolerance.

The SDS tolerant soybean plant or germplasm may be the progeny of an introgression wherein the recurrent parent is an elite variety of soybean and the donor comprises an allele associated with enhanced SDS tolerance.

The SDS tolerant soybean plant or germplasm may be the progeny of a cross between a first elite variety of soybean (e.g., a tester line) and the progeny of a cross between a second elite variety of soybean (e.g., a recurrent parent) and a variety of soybean that comprises an allele associated with enhanced SDS tolerance (e.g., a donor).

The SDS tolerant soybean plant or germplasm may be the progeny of a cross between a first elite variety of soybean and the progeny of an introgression wherein the recurrent parent is a second elite variety of soybean and the donor comprises an allele associated with enhanced SDS tolerance.

An SDS tolerant soybean plant and germplasm of the present invention may comprise one or more markers of the present invention.

In some embodiments, the SDS tolerant soybean plant or germplasm may comprise within its genome, a marker associated with enhanced SDS tolerance, wherein said marker is located within a chromosomal interval selected from the group consisting of:
1. a chromosomal interval defined by and including a C allele at SY0302B and a T allele at SY0303A;
2. a chromosomal interval defined by and including a G allele or an A allele at SY0060A and a C allele at SY0906A;
3. a chromosomal interval defined by and including a T allele at SY0946A and a T allele at SY1005A;
4. a chromosomal interval defined by and including an A allele or a T allele at SY1032A and an insertion at SY0421A;
5. a chromosomal interval defined by and including a C allele at SY0118B and an A allele at SY0126C;
6. a chromosomal interval defined by and including a T allele at SY1090A and a C allele or a T allele at SY0098B;
7. a chromosomal interval defined by and including an A allele or a C allele at SY0992A and a T allele at SY1324A;
8. a chromosomal interval defined by and including a C allele at SY0632A and a T allele at SY0634B; and
9. any combination of (1) through (8) above.

In some embodiments, the SDS tolerant soybean plant or germplasm may comprise within its genome a marker that comprises, consists essentially of or consists of marker alleles located in at least two different chromosomal intervals. For example, the marker may comprise one or more alleles located in the chromosomal interval defined by and including SY0007A and SY1324A and one or more alleles located in the chromosomal interval defined by and including SY0871A and SY0098B.

In some embodiments, the SDS tolerant soybean plant or germplasm may comprise within its genome, a marker associated with enhanced SDS tolerance, wherein said marker is selected from the group consisting of:
1. a C allele at SY0302B;
2. a T allele at SY0303A;
3. a G allele or an A allele at SY0060A;
4. a C allele at SY0906A;
5. a T allele at SY0946A;
6. a T allele at SY0916A;
7. a T allele at SY1005A;
8. an A allele at SY1032A;
9. a T allele at SY0132A;
10. a C allele at SY0422A;
11. a T allele at SY0080A;
12. an insertion at SY0421A;
13. a C allele at SY0118B;
14. a C allele at SY0121A;
15. a G allele at SY0125B;
16. an A allele at SY0126C;
17. a T allele at SY1090A;
18. an A allele or a T allele at SY0871A;
19. a T allele or a C allele at SY0096A;
20. an A allele or a T allele at SY0567A;
21. a C allele or a T allele at SY0098B;
22. a T allele at SY0346B;
23. an A allele or a C allele at SY0992A;
24. a G allele or a T allele at SY0007A;
25. a G allele at SY0007B;
26. a T allele at SY0445A;
27. a T allele at SY1324A;
28. a C allele at SY0632A;
29. a T allele at SY1003A;
30. a G allele at SY0635A;
31. an A allele at SY0636A;
32. a C allele at SY0984A;
33. a T allele at SY0634B; and
34. any combination of (1) through (33) above.

In some embodiments, the SDS tolerant soybean plant or germplasm may comprise within its genome, a marker associated with enhanced SDS tolerance, wherein said marker is selected from the group consisting of:
1) a T allele at SY0303A;
2) a C allele at SY0906A;
3) a T allele at SY0946A;
4) a T allele at SY0080A;
5) a C allele at SY0121A;
6) a C allele or a T allele at SY0098B;
7) a T allele at SY0346B;
8) a G allele or a T allele at SY0007A;
9) a C allele at SY0984A; and
10) any combination of (1) through (9) above.

SDS Tolerant Soybean Seeds

The present invention provides SDS tolerant soybean seeds. As discussed above, the methods of the present invention may be utilized to identify, produce and/or select an SDS tolerant soybean seed. In addition to the methods described above, an SDS tolerant soybean seed may be produced by any method whereby a marker associated with enhanced SDS tolerance is introduced into the soybean seed, including, but not limited to, transformation, protoplast transformation or fusion, a double haploid technique, embryo rescue, and/or by any other nucleic acid transfer system.

In some embodiments, the SDS tolerant soybean seed comprises a non-naturally occurring variety of soybean. In some embodiments, the soybean seed is at least about 50%, 55%, 60%, 65%, 70%, 75%, 80%, 85%, 90%, 95%, 97%, 99% or 100% identical to that of an elite variety of soybean.

The SDS tolerant soybean seed may be produced by an SDS tolerant soybean plant identified, produced or selected by the methods of the present invention. In some embodiments, the SDS tolerant soybean seed is produced by an SDS tolerant soybean plant of the present invention.

An SDS tolerant soybean seed of the present invention may comprise one or more markers of the present invention.

In some embodiments, the SDS tolerant soybean seed may comprise within its genome, a marker associated with enhanced SDS tolerance, wherein said marker is located within a chromosomal interval selected from the group consisting of:
1. a chromosomal interval defined by and including a C allele at SY0302B and a T allele at SY0303A;
2. a chromosomal interval defined by and including a G allele or an A allele at SY0060A and a C allele at SY0906A;
3. a chromosomal interval defined by and including a T allele at SY0946A and a T allele at SY1005A;
4. a chromosomal interval defined by and including an A allele or a T allele at SY1032A and an insertion at SY0421A;
5. a chromosomal interval defined by and including a C allele at SY0118B and an A allele at SY0126C;
6. a chromosomal interval defined by and including a T allele at SY1090A and a C allele or a T allele at SY0098B;
7. a chromosomal interval defined by and including an A allele or a C allele at SY0992A and a T allele at SY1324A;

8. a chromosomal interval defined by and including a C allele at SY0632A and a T allele at SY0634B; and
9. any combination of (1) through (8) above.

In some embodiments, the SDS tolerant soybean seed may comprise within its genome a marker that comprises, consists essentially of or consists of marker alleles located in at least two different chromosomal intervals. For example, the marker may comprise one or more alleles located in the chromosomal interval defined by and including SY0007A and SY1324A and one or more alleles located in the chromosomal interval defined by and including SY0871A and SY0098B.

In some embodiments, the SDS tolerant soybean seed may comprise within its genome, a marker associated with enhanced SDS tolerance, wherein said marker is selected from the group consisting of:
1. a C allele at SY0302B;
2. a T allele at SY0303A;
3. a G allele or an A allele at SY0060A;
4. a C allele at SY0906A;
5. a T allele at SY0946A;
6. a T allele at SY0916A;
7. a T allele at SY1005A;
8. an A allele at SY1032A;
9. a T allele at SY0132A;
10. a C allele at SY0422A;
11. a T allele at SY0080A;
12. an insertion at SY0421A;
13. a C allele at SY0118B;
14. a C allele at SY0121A;
15. a G allele at SY0125B;
16. an A allele at SY0126C;
17. a T allele at SY1090A;
18. an A allele or a T allele at SY0871A;
19. a T allele or a C allele at SY0096A;
20. an A allele or a T allele at SY0567A;
21. a C allele or a T allele at SY0098B;
22. a T allele at SY0346B;
23. an A allele or a C allele at SY0992A;
24. a G allele or a T allele at SY0007A;
25. a G allele at SY0007B;
26. a T allele at SY0445A;
27. a T allele at SY1324A;
28. a C allele at SY0632A;
29. a T allele at SY1003A;
30. a G allele at SY0635A;
31. an A allele at SY0636A;
32. a C allele at SY0984A;
33. a T allele at SY0634B; and
34. any combination of (1) through (33) above.

In some embodiments, the SDS tolerant soybean seed may comprise within its genome, a marker associated with enhanced SDS tolerance, wherein said marker is selected from the group consisting of:
1) a T allele at SY0303A;
2) a C allele at SY0906A;
3) a T allele at SY0946A;
4) a T allele at SY0080A;
5) a C allele at SY0121A;
6) a C allele or a T allele at SY0098B;
7) a T allele at SY0346B;
8) a G allele or a T allele at SY0007A;
9) a C allele at SY0984A; and
10) any combination of (1) through (9) above.

EXAMPLES

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

Example 1

Approximately 1,071 soybean lines were grown in different locations—St. Joseph, Ill.; Highland, Ill.; Monterey, Ind.; Fairbank, Iowa; Slater, Iowa—and exposed to *Fusarium solani*. Each line was grown in three of the locations (50 plants per repetition for 2 repetitions at each site) and evaluated for its SDS response. Plants were scored approximately once per week for 3 to 4 weeks based upon the incidence and severity of SDS symptoms according to the following scale (note scale was also used in second experiment discussed starting with Example 6):
1=no SDS symptoms
2=about 10% of the plants show symptoms with low level severity
3=about 25% of the plants show symptoms with low to some moderate severity
4=about 40% of the plants show symptoms with low to moderate severity
5=about 50% of the plants show symptoms with moderate severity
6=about 60% of the plants show symptoms with moderate to some high severity
7=about 75% of the plants show symptoms with moderate to high severity
8=about 90% of the plants show symptoms with high severity
9=all of the plants are dead from SDS.

Each of the soybean lines was genotyped with respect to approximately 1,000 SNP markers, and associations between SDS response and the SNP markers were detected using q+K linear mixed models for each location. See Yu et al. NATURE GENETICS 38:203 (2006).

P-value-based meta-analysis was performed across locations to identify markers associated with SDS tolerance and potential quantitative trait loci (QTLs). A marker allele was deemed to be significantly associated with SDS tolerance if it had a combined p-value (across locations) of less than or equal to $4.37 \times 10^{-5}$, which was equivalent to a genome-wide type I error of 5%.

Table 3 describes marker alleles from this study that were determined to be significantly associated with SDS tolerance.

TABLE 3

List of markers identified in Example 1.

| Marker Locus | Physical Map Position in Glyma 1.01 (chromosome) nucleotide | Marker Allele |
| --- | --- | --- |
| SY0302B | (1) 2,699,816 | C |
| SY0303A | (1) 2,840,660 | T |
| SY0060A | (3) 36,490,923 | G |
| SY0060A | (3) 36,490,923 | A |
| SY0906A | (3) 46,058,803 | C |
| SY0946A | (6) 12,950,865 | T |
| SY0916A | (6) 16,155,152 | T |
| SY1005A | (6) 27,068,199 | T |
| SY1032A | (13) 20,484,995 | A |

TABLE 3-continued

List of markers identified in Example 1.

| Marker Locus | Physical Map Position in Glyma 1.01 (chromosome) nucleotide | Marker Allele |
|---|---|---|
| SY0132A | (13) 29,825,027 | T |
| SY0422A | (13) 29,825,175 | C |
| SY0080A | (13) 30,457,450 | T |
| SY0421A | (13) 30,965,274 | I |
| SY0118B | (14) 807,326 | C |
| SY0121A | (14) 1,359,785 | C |
| SY0125B | (14) 1,877,090 | G |
| SY0126C | (14) 2,104,413 | A |
| SY1090A | (16) 26,959,365 | T |
| SY0871A | (16) 31,869,001 | A |
| SY0871A | (16) 31,869,001 | T |
| SY0096A | (16) 32,101,062 | T |
| SY0096A | (16) 32,101,062 | C |
| SY0567A | (16) 32,881,385 | A |
| SY0567A | (16) 32,881,385 | T |
| SY0098B | (16) 32,881,404 | C |
| SY0098B | (16) 32,881,404 | T |
| SY0346B | (17) 19,056,429 | T |
| SY0992A | (18) 1,231,629 | A |
| SY0992A | (18) 1,231,629 | C |
| SY0007A | (18) 1,736,100 | G |
| SY0007A | (18) 1,736,100 | T |
| SY0007B | (18) 1,736,136 | G |
| SY0445A | (18) 2,042,727 | T |
| SY1324A | (18) 2,833,147 | T |
| SY0632A | (19) 48,091,800 | C |
| SY1003A | (19) 48,609,911 | T |
| SY0635A | (19) 49,845,462 | G |
| SY0636A | (19) 50,222,617 | A |
| SY0984A | (19) 50,414,093 | C |
| SY0634B | (19) 50,424,620 | T |

Example 2

A DNA sample from a soybean plant is assayed for the presence of a marker associated with SDS tolerance (e.g., one or more of the desired alleles described in Table 3). Upon detecting the marker in the DNA sample, the soybean plant is identified as being an SDS tolerant soybean plant.

Example 3

A DNA sample from a soybean germplasm is assayed for the presence of a marker associated with SDS tolerance (e.g., one or more of the desired alleles described in Table 3). Upon detecting the marker in the DNA sample, the soybean germplasm is identified as being an SDS tolerant soybean germplasm. A soybean plant is produced from the SDS tolerant soybean germplasm, thereby producing an SDS tolerant soybean plant.

Example 4

A first variety of soybean comprising a marker associated with SDS tolerance (e.g., one or more of the desired alleles described in Table 3) is crossed with a second variety of soybean lacking the marker. DNA samples from progeny plants are assayed for the presence of the marker. Progeny plants whose corresponding DNA samples comprise the marker are selected.

Example 5

A first variety of soybean comprising a marker associated with SDS tolerance (e.g., one or more of the desired alleles described in Table 3) is crossed with a second variety of soybean lacking the marker. Progeny comprising the marker are repeatedly backcrossed with the second variety of soybean, thereby producing a soybean plant wherein the marker has been introgressed into the genetic background of the second variety of soybean.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

Example 6

A second set of experiments were carried out to identify further markers associated with increased resistance to SDS.

SDS tolerant varieties are widely distributed in the breeding program spanning maturity groups 3 and 4 where SDS is prevalent, thus; marker trait associations "MTA" using internal germplasm was used. Two approaches were utilized to identify quantitative trait loci (QTL) for SDS tolerance: 1) bulk segregant analysis (BSA) and 2) network population mapping (NPM):

BSA: Is a rapid mapping strategy, which does not need to develop a genetic linkage map. In this case, artificial bi-parental populations were created using tolerant and susceptible lines. The essence of this procedure is to create two bulk DNA samples, one containing DNA from plants that are tolerant to SDS and a second bulk containing DNA from plants that are susceptible to SDS.

NPM: SDS tolerant populations, which are connected via shared parents, allow the evaluation of multiple alleles at multiple genetic backgrounds using series of connected crosses together. Thus, NPM has the advantage of determining gene effects on multiple genetic backgrounds.

Bulk Segregant Analysis (BSA)

Two bi-parental populations were developed using two SDS tolerant parents, S39-A3 and UA4805 which are widely used in SDS breeding programs. The pedigree of the two populations created is presented in Table 4. Each population had 180 progeny. The F5:6 population of each crossing generated phenotyping data from field trials. Based on a disease severity score, 10 to 20 most tolerant and 10 to 20 most susceptible progeny were selected per population and DNA of the lines was bulked for a tolerant pool and a susceptible pool. Two distinct pools were sequenced by short read sequencing technology known as Illumina sequencing (see. E.g. www.illumina.com/technology/next-generation-sequencing/sequencing-technology). The sequencing was conducted at the national center for genome resources and results were analyzed.

The two same bi-parental populations were also utilized to map QTL using existing phenotyping data (disease severity) and newly generated phenotype data (disease severity (DS) and disease incidence (DI)).

TABLE 4

Summary of two populations developed for BSA

| | | Tolerant parent | | Susceptible parent | |
|---|---|---|---|---|---|
| Population | Pedigree | | SDS Score | | SDS Score |
| MG* 3 | S36-B6 × S39-A3 | S39-A3 | 2 | S36-B6 | 8 |
| MG 4 | UA4805 × S46-U6 | UA4805** | 2 | S46-U6 | 6 |

*MG = maturity group
**Conventional variety developed by U of Arkansas released in 2005

Network Population Mapping (NPM)

A total of 4 maturity group 3 and 4 maturity group 4 populations connected with common parent lines were developed for NPM. Two SDS tolerant lines per maturity group 3 and 4 were utilized as common parents and their mean SDS score is 2.65 and 3.2, respectively (Table 2). The populations' size was 96 progeny per crossing. At F5:6, each population was screened to generate genotypic data using ~900 polymorphic markers which span the whole soybean genome. Two phenotypic data were collected (DS and DI) in two locations per group in 2012. Multiple ratings up to 4 readings were taken over a course of 3-4 weeks starting at R2-R6. Each experiment per group included nine common checks (four tolerant and five susceptible checks).

Example 7

Validation Study for BSA and NPM SDS Markers

In order to validate QTL and associated markers identified by BSA and NPM, a QTL validation experiment was conducted. A total of 147 lines of stage 4 and above representing maturity group 3 and 4 were phenotyped at four locations (Slater, Iowa, St. Joe, Ill., Monterey, Ind. and Valmeyer, Ill.). All lines were phenotyped for DS and DI. Genotypes were generated using markers representing the QTL derived from the combined results of BSA and NPM.

Results

Bulk Segregant Analysis (BSA)

A BSA experiment using materials derived from maturity group 3 (S36-B6×S39-A3) was conducted successfully. Three QTL were identified on linkage group K, H and J, chromosome 9, 12 and 16, respectively. As a function of the sequence BSA approach, the high number of significant variants identified on QTL linkage group J compared to other two QTL which suggests the QTL on linkage group J is the strongest QTL. Interestingly, there were several predicted genes within the QTL on chromosome 16; physical position ranges from 31,112,859 bp to 33,364,137 bp. This region annotated as disease resistant genes based on sequence homology such as TIR-NBS-LRR class repetition.

In contrast, the BSA experiment using materials derived from maturity group 4 (UA4805×S46-U6) did not detect statistically meaningful QTL.

Example 8

QTL mappings were conducted using two sets of phenotypic data: 1) DS generated internally and 2) disease index (DX) generated at the Southern Illinois University. DX was calculated from DI and DS, using the formula: DX=DI×DS/9, and it has a range of 0 (no disease) to 100 (all plants prematurely dead at or before R6). Both analyses using DS and DX detected the same QTL on linkage group J (chromosome 16: 31,075727 bp to 35,175,117 bp) which was also detected by BSA experiment in section 4.1. The phenotypic variation explained by the QTL was 50.7%.

Network Population Mapping (NPM)

NPM mapping was conducted using only severity score because incidence scores from Monterey, Ind. and Valmeyer, Ill. were low, 38% and 62% per plot, respectively. The severity scores of all 8 populations were evaluated for quality checking. In order to improve statistical detection power, NPM was conducted using all 8 populations. A QTL was detected on linkage group L using severity trait collected from three different locations. The phenotypic variation explained by this QTL was 24%.

By combining the results from the BSA, two bi-parental and eight NPM mapping populations, QTL from two chromosomes were prioritized and summarized in Table 5 for implementation.

TABLE 5

Markers that associate with SDS resistance

| Linkage group | Genetic position | Marker | Beneficial allele | Unbeneficial allele | LOD | $R^2$ (%) |
|---|---|---|---|---|---|---|
| J | 139.9 cM | SY0086A | CC | AA | 4.41 | 23.03 |
| J | 155.2 cM | SY0567A | AA | TT | 2.64 | 50.72 |
| J | 158 cM | SY0004A | CC | GG | 2.92 | 26.97 |
| L | 160.6 cM | SY2798 | AA | GG | 3.44 | 23.49 |
| L | 160.6 cM | SY1036A | AA | GG | 3.44 | 23.49 |

Example 9

Metabolite Profiling

Metabolite profiling was conducted using three tolerant and three susceptible lines derived from BSA maturity group 3 population in Metabolon (www.metabolon.com/). A total of 15 metabolic compounds were found. Salicylate was the top named compound by statistical analysis which is a known hormonal regulator of disease responses in plants, and produces anti-microbial compounds such as phytoalexins. Several additional compounds in the phenylpropanoid pathways in addition to salicylate were consistently higher in populations scoring as SDS tolerant lines. Additionally, there were high levels of dipeptide pools and lower levels of tryptophan, an aminao acid that is a precursor for the plant hormone, auxin. From these findings a list of markers associating with the salicylate pathway were generated and included as markers that, not to be limited in theory, may associate with SDS resistance in a soy plant.

What is claimed is:

1. A method of selecting a soybean plant having increased tolerance to Soybean Sudden Death Syndrome (SDS), the method comprising the steps of:
    a) isolating a nucleic acid from a soybean cell or plant part;
    b) detecting, in said nucleic acid the presence of a marker associated with increased SDS tolerance, wherein said marker is located within a chromosomal interval on soybean chromosome 1 corresponding to physical positions 2,699,816 to 2,840,660, wherein said chromosomal interval comprises either one of marker locus SY0302B located at physical position 2,699,816, wherein said marker locus comprises a C; or marker locus SY0303A located at physical position 2,840,660, wherein said marker locus comprises a T;
    c) selecting said plant on the basis of the presence of the marker detected in b); and
    d) crossing said selected plant with a second soybean plant lacking the SDS tolerant marker locus to produce progeny plants having tolerance to SDS.

2. The method of claim 1, wherein detection is carried out by PCR amplification.

3. The method of claim 1, wherein said soybean plant is *Glycine max*.

4. A method of producing a soybean plant having increased resistance to Soybean Sudden Death Syndrome (SDS), the method comprising the steps of:
    a) isolating a nucleic acid from a first soybean plant;
    b) detecting, in said first soybean plant the presence of a marker associated with increased SDS tolerance, wherein said marker is located within a chromosomal interval on soybean chromosome 1 corresponding to physical positions 2,699,816 to 2,840,660, wherein said chromosomal interval comprises either one of marker locus SY0302B located at physical position 2,699,816, wherein said marker locus comprises a C; or marker locus SY0303A located at physical position 2,840,660, wherein said marker locus comprises a T;

c) crossing the first soybean plant of b) with a second soybean plant not comprising said marker; and d) producing a progeny plant from the cross of c), wherein said progeny plant comprises the marker detected in b), thereby producing a plant with increased resistance to SDS.

5. The method of claim 4, further comprising the steps:

(d) crossing the progeny soybean plant that comprises said marker within its genome with itself or another soybean plant to yield additional progeny soybean plants comprising the marker within their genome; and (e) repeating the crossing step of (d) at least 2 times to generate further progeny soybean plants comprising the marker within their genome.

6. The method of claim 4, wherein detection is carried out by PCR amplification.

7. The method of claim 4, wherein said soybean plant is *Glycine max*.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Glycine Max

```
<400> SEQUENCE: 1
tccgaacatg gttggtt                                                  17

<210> SEQ ID NO 2
<211> LENGTH: 20
<212> TYPE: DNA
<213> ORGANISM: Glycine Max

<400> SEQUENCE: 2
aaactggacc tcactttacc                                               20

<210> SEQ ID NO 3
<211> LENGTH: 16
<212> TYPE: DNA
<213> ORGANISM: Glycine Max

<400> SEQUENCE: 3
ccaatctaaa cccgaa                                                   16

<210> SEQ ID NO 4
<211> LENGTH: 20
<212> TYPE: DNA
<213> ORGANISM: Glycine Max

<400> SEQUENCE: 4
tgggagaggg actcttgaga                                               20

<210> SEQ ID NO 5
<211> LENGTH: 24
<212> TYPE: DNA
<213> ORGANISM: Glycine Max

<400> SEQUENCE: 5
tcgaacaaaa ggacttacac agaa                                          24

<210> SEQ ID NO 6
<211> LENGTH: 17
<212> TYPE: DNA
<213> ORGANISM: Glycine Max

<400> SEQUENCE: 6
tacttgccaa ttccaga                                                  17
```